US007524456B1

(12) United States Patent
Buechler

(10) Patent No.: US 7,524,456 B1
(45) Date of Patent: *Apr. 28, 2009

(54) DIAGNOSTIC DEVICES FOR THE CONTROLLED MOVEMENT OF REAGENTS WITHOUT MEMBRANES

(75) Inventor: Kenneth F. Buechler, San Diego, CA (US)

(73) Assignee: Biosite Incorporated, San Diego, CA (US)

( * ) Notice: Subject to any disclaimer, the term of this patent is extended or adjusted under 35 U.S.C. 154(b) by 81 days.

This patent is subject to a terminal disclaimer.

(21) Appl. No.: 09/613,650

(22) Filed: Jul. 11, 2000

Related U.S. Application Data

(60) Continuation-in-part of application No. 08/828,041, filed on Mar. 27, 1997, now Pat. No. 6,156,270, which is a continuation-in-part of application No. 08/447,895, filed on May 23, 1995, now Pat. No. 6,019,944, which is a division of application No. 08/065,528, filed on May 19, 1993, now abandoned, which is a continuation-in-part of application No. 07/887,526, filed on May 21, 1992, now Pat. No. 5,458,852, application No. 09/613,650, which is a continuation-in-part of application No. 08/810,569, filed on Mar. 3, 1997, now Pat. No. 6,143,576, which is a continuation-in-part of application No. 08/447,981, filed on May 23, 1995, now Pat. No. 5,885,527, which is a division of application No. 08/065,528, filed on May 19, 1993, now abandoned, which is a continuation-in-part of application No. 07/887,526, filed on May 21, 1992, now Pat. No. 5,458,852, application No. 09/613,650, which is a continuation-in-part of application No. 08/902,775, filed on Jul. 30, 1997, now Pat. No. 6,271,040, which is a continuation-in-part of application No. 08/810,569, filed on Mar. 3, 1997, now Pat. No. 6,143,576.

(51) Int. Cl.
*G01N 33/48* (2006.01)

(52) U.S. Cl. .......................... 422/58; 422/61; 422/102; 436/165; 436/177

(58) Field of Classification Search .................. 422/58, 422/61, 82.05, 100, 102, 73; 436/524, 531, 436/533, 165, 177
See application file for complete search history.

(56) References Cited

U.S. PATENT DOCUMENTS 3,966,897 A * 6/1976 Renn et al. ................... 436/515

(Continued)

FOREIGN PATENT DOCUMENTS

EP         0 418 765 A2    3/1991

(Continued)

OTHER PUBLICATIONS

Phadke, "Biosensors and enzyme immobilized electrodes." Biosystems, 27:203-206, 1992.

(Continued)

*Primary Examiner*—Lyle A Alexander
(74) *Attorney, Agent, or Firm*—Wilson Sonsini Goodrich & Rosati

(57) ABSTRACT

The assay devices, assay systems and device components of this invention comprise at least two opposing surfaces disposed a capillary distance apart, at least one of which is capable of immobilizing at least one target ligand or a conjugate in an amount related to the presence or amount of target ligand in the sample from a fluid sample in a zone for controlled fluid movement to, through or away the zone. The inventive device components may be incorporated into conventional assay devices with membranes or may be used in the inventive membrane-less devices herein described and claimed. These components include flow control elements, measurement elements, time gates, elements for the elimination of pipetting steps, and generally, elements for the controlled flow, timing, delivery, incubation, separation, washing and other steps of the assay process.

20 Claims, 18 Drawing Sheets

U.S. PATENT DOCUMENTS

| | | | |
|---|---|---|---|
| 4,233,029 A | 11/1980 | Columbus | 422/58 |
| 4,426,451 A | 1/1984 | Columbus | 436/518 |
| 4,435,504 A | 3/1984 | Zuk et al. | 435/7 |
| 4,591,570 A | 5/1986 | Chang | |
| 4,647,543 A * | 3/1987 | Stocker | 436/174 |
| 4,695,554 A | 9/1987 | O'Connell et al. | |
| 4,727,019 A | 2/1988 | Valkirs et al. | |
| 4,756,828 A | 7/1988 | Litman et al. | 435/7 |
| 4,756,884 A | 7/1988 | Hillman et al. | 422/68 |
| 4,757,004 A | 7/1988 | Houts et al. | 435/7 |
| 4,829,010 A | 5/1989 | Chang | |
| 4,857,453 A | 8/1989 | Ullman et al. | 435/7 |
| 4,859,613 A | 8/1989 | Lawrence | |
| 4,877,586 A | 10/1989 | Devaney, Jr. et al. | |
| 4,879,215 A | 11/1989 | Weng et al. | 435/7 |
| 4,883,688 A | 11/1989 | Houts et al. | 427/285 |
| 4,906,439 A | 3/1990 | Grenner | 422/56 |
| 4,911,782 A | 3/1990 | Brown | |
| 4,916,056 A | 4/1990 | Brown, III et al. | 435/7 |
| 4,945,205 A | 7/1990 | Litman et al. | 219/121 |
| 4,948,961 A | 8/1990 | Hillman et al. | 250/252.1 |
| 4,960,691 A | 10/1990 | Gordon et al. | 435/6 |
| 4,963,498 A | 10/1990 | Hillman et al. | 436/69 |
| 4,978,503 A | 12/1990 | Shanks et al. | |
| 5,004,923 A | 4/1991 | Hillman et al. | 250/341 |
| 5,006,309 A | 4/1991 | Khalil et al. | 422/56 |
| 5,023,054 A | 6/1991 | Sato et al. | 422/82.09 |
| 5,028,535 A | 7/1991 | Buechler et al. | 435/7.1 |
| 5,051,237 A | 9/1991 | Grenner et al. | 422/56 |
| 5,087,556 A | 2/1992 | Ertinghausen | 422/56 |
| 5,089,391 A | 2/1992 | Buechler et al. | 435/7.1 |
| 5,091,318 A * | 2/1992 | Anawis et al. | 436/513 |
| 5,137,808 A | 8/1992 | Ullman et al. | 422/56 |
| 5,140,161 A | 8/1992 | Hillman et al. | 250/341 |
| 5,144,139 A | 9/1992 | Hillman et al. | 250/341 |
| 5,147,607 A | 9/1992 | Mochida | 422/57 |
| 5,155,212 A | 10/1992 | Dubler et al. | |
| 5,164,598 A | 11/1992 | Hillman et al. | 250/341 |
| 5,202,268 A | 4/1993 | Kuhn et al. | |
| 5,204,525 A | 4/1993 | Hillman et al. | 250/252.1 |
| 5,209,904 A | 5/1993 | Forney et al. | 422/73 |
| 5,300,779 A | 4/1994 | Hillman et al. | 250/341 |
| 5,387,510 A | 2/1995 | Wu | |
| 5,437,983 A * | 8/1995 | Watts et al. | 436/533 |
| 5,445,970 A * | 8/1995 | Rohr | 436/526 |
| 5,458,852 A | 10/1995 | Buechler | 422/58 |
| 5,486,335 A | 1/1996 | Wilding et al. | |
| 5,512,659 A * | 4/1996 | Ullman et al. | 530/391.1 |
| 5,514,550 A | 5/1996 | Findlay et al. | |
| 5,766,961 A | 6/1998 | Pawiak et al. | |
| 5,885,527 A | 3/1999 | Buechler | 422/58 |
| 5,888,723 A * | 3/1999 | Sutton et al. | 436/533 |
| 5,922,615 A | 7/1999 | Nowakowski et al. | |
| 6,019,944 A | 2/2000 | Buechler | 422/58 |
| 6,040,193 A * | 3/2000 | Winkler et al. | 436/180 |
| 6,156,270 A | 12/2000 | Buechler | |

FOREIGN PATENT DOCUMENTS

| | | |
|---|---|---|
| EP | 0 212 314 B1 | 4/1994 |
| EP | 0 695 941 | 2/1996 |
| EP | 0 348 006 B2 | 10/1997 |
| JP | A-57-113364 | 7/1982 |
| JP | A-57-156028 | 9/1982 |
| JP | A-62-129759 | 6/1987 |
| JP | A-1-203038 | 8/1989 |
| JP | A-3-223674 | 10/1991 |
| WO | WO 94/09366 | 4/1994 |
| WO | WO 97/00442 | 1/1997 |
| WO | WO 97/02357 | 1/1997 |

OTHER PUBLICATIONS

Rogers et al., "biosensors for environmental monitoring." *Biosensors & Bioelectronics*, 7:317-321, 1992.

Cambridge Dictionary of Science and Technology, (Peter M.B. Walker, Gen. Ed.), New York, NY, p. 131 (1988) (Reprinted 1990).

K.A. Dill, "Dominant Forces in Protein Folding," *Biochemistry*, 29(31):7133-7155 (1990).

G. Frens, "Controlled Nucleation of the Regulation of the Particle Size in Monodisperse Gold Suspensions," *Nature Physical Science*, 241:20-22 (1973).

Laibinis, et al., "ω-Terminated Alkanethiolate Monolayers on Surfaces of Copper, Silver, and Gold Have Similar Wettabilities," *J. Am. Chem. Soc.*, 114:1990-1995 (1992).

Lou, et al., "One-Step Competitive Immunochromatographic Assay for Semiquantitative Determination of Lipoprotein(a) in Plasma," *Clin. Chem.*, 39(4):619-624 (1993).

D. Myers, "Surfaces, Interfaces, and Colloids—Principles and Applications," (VCH Publishers, Inc.), New York, NY (1991).

Ross, et al., "Thermodynamics of Protein Association Reactions: Forces Contributing to Stability," *Biochemistry*, 20:3096-3102 (1981).

* cited by examiner

CONCAVE FLOW FRONT

CONVEX FLOW FRONT

DIAGNOSTIC DEVICES FOR THE CONTROLLED MOVEMENT OF REAGENTS WITHOUT MEMBRANES

This application is a continuation-in-part of U.S. patent application Ser. No. 08/828,041, now U.S. Pat. No. 6,156,270, which is a continuation in part of U.S. patent application Ser. No. 08/447,895, which issued as U.S. Pat. No. 6,019,944 on Feb. 1, 2000, which is a divisional applications of U.S. patent application Ser. No. 08/065,528 (abandoned), filed 19 May 1993, which was a continuation-in-part of U.S. patent application Ser. No. 07/887,526 filed 21 May 1992 which issued as U.S. Pat. No. 5,458,852 on Oct. 17, 1995; U.S. patent application Ser. No. 08/810,569, now U.S. Pat. No. 6,143,576 which is a continuation in part of U.S. patent application Ser. No. 08/447,981, which issued as U.S. Pat. No. 5,885,527 on Mar. 23, 1999, which is a divisional application of U.S. patent application Ser. No. 08/065,528 (abandoned), filed 19 May 1993, which was a continuation-in-part of U.S. patent application Ser. No. 07/887,526 filed 21 May 1992 which issued as U.S. Pat. No. 5,458,852 on Oct. 17, 1995; and U.S. patent application Ser. No. 08/902,775, now U.S. Pat. No. 6,274,040 which is a continuation in part of U.S. patent application Ser. No. 08/810,569, now U.S. Pat. No. 6,143,576, from each of which priority is claimed, and each of which is fully incorporated by reference herein.

FIELD OF THE INVENTION

This invention relates to devices for conducting assays, including qualitative, semi-quantitative and quantitative determinations of one or more analytes in a single test format.

BACKGROUND OF THE INVENTION

Over the years, numerous simplified test systems have been designed to rapidly detect the presence of a target ligand of interest in biological, environmental and industrial fluids. A synonym for target ligand is analyte or target analyte. In one of their simplest forms, these assay systems and devices usually involve the combination of a test reagent which is capable of reacting with the target ligand to give a visual response and an absorbent paper or membrane through which the test reagents flow. Paper products, glass fibers and nylon are commonly used for the absorbent materials of the devices. In certain cases, the portion of the absorbent member containing the test reagents is brought into contact, either physically or through capillarity, with the sample containing the target ligand. The contact may be accomplished in a variety of ways. Most commonly, an aqueous sample is allowed to traverse a porous or absorbent member, such as porous polyethylene or polypropylene or membranes by capillarity through the portion of the porous or absorbent member containing the test reagents. In other cases, the test reagents are pre-mixed outside the test device and then added to the absorbent member of the device to ultimately generate a signal.

Commercially available diagnostic products employ a concentrating zone methodology. In these products, such as ICON$^R$ (Hybritech Incorporated), TESTPACK™ (Abbott Laboratories) or ACCULEVEL$^R$ (Syva Corporation), the device contains an immunosorbing or capture zone within a porous member to which a member of a specific binding pair is immobilized. The surface of the porous member also may be treated to contain one or more elements of a signal development system. In these devices, there is a liquid absorbing zone which serves to draw liquid through the immunosorbing zone, to absorb liquid sample and reagents and to control the rate at which the liquid is drawn through the immunosorbing zone. The liquid absorbing zone is either an additional volume of the porous member outside of the immunosorbing zone or an absorbent material in capillary communication with the immunosorbing zone. Many commercially available devices and assay systems also involve a wash step in which the immunosorbing zone is washed free of nonspecifically bound signal generator so that the presence or amount of target ligand in the sample can be determined by examining the porous member for a signal at the appropriate zone.

In addition to the limitations of the assay devices and systems of the prior art, including the limitations of using absorbent membranes as carriers for sample and reagents, assay devices generally involve numerous steps, including critical pipetting steps which must be performed by relatively skilled users in laboratory settings. Accordingly, there is a need for one step assay devices and systems, which, in addition to controlling the flow of reagents in the device, control the timing of the flow of reagents at specific areas in the device. In addition, there is a need for assay devices which do not require critical pipetting steps but still perform semi-quantitative and quantitative determinations.

DESCRIPTION OF THE DRAWINGS

FIGS. 12A, 12C and 12E depict various embodiments without a lid attached; FIG. 12B depicts an embodiment of FIG. 12A with a lid attached, FIG. 12D depicts an embodiment of FIG. 12C with a lid attached, FIG. 12F depicts an embodiment of FIG. 12E with a lid attached. The energy directors and stops in FIG. 12 can be configured as posts or ridges.

SUMMARY OF THE INVENTION

Figure 1:
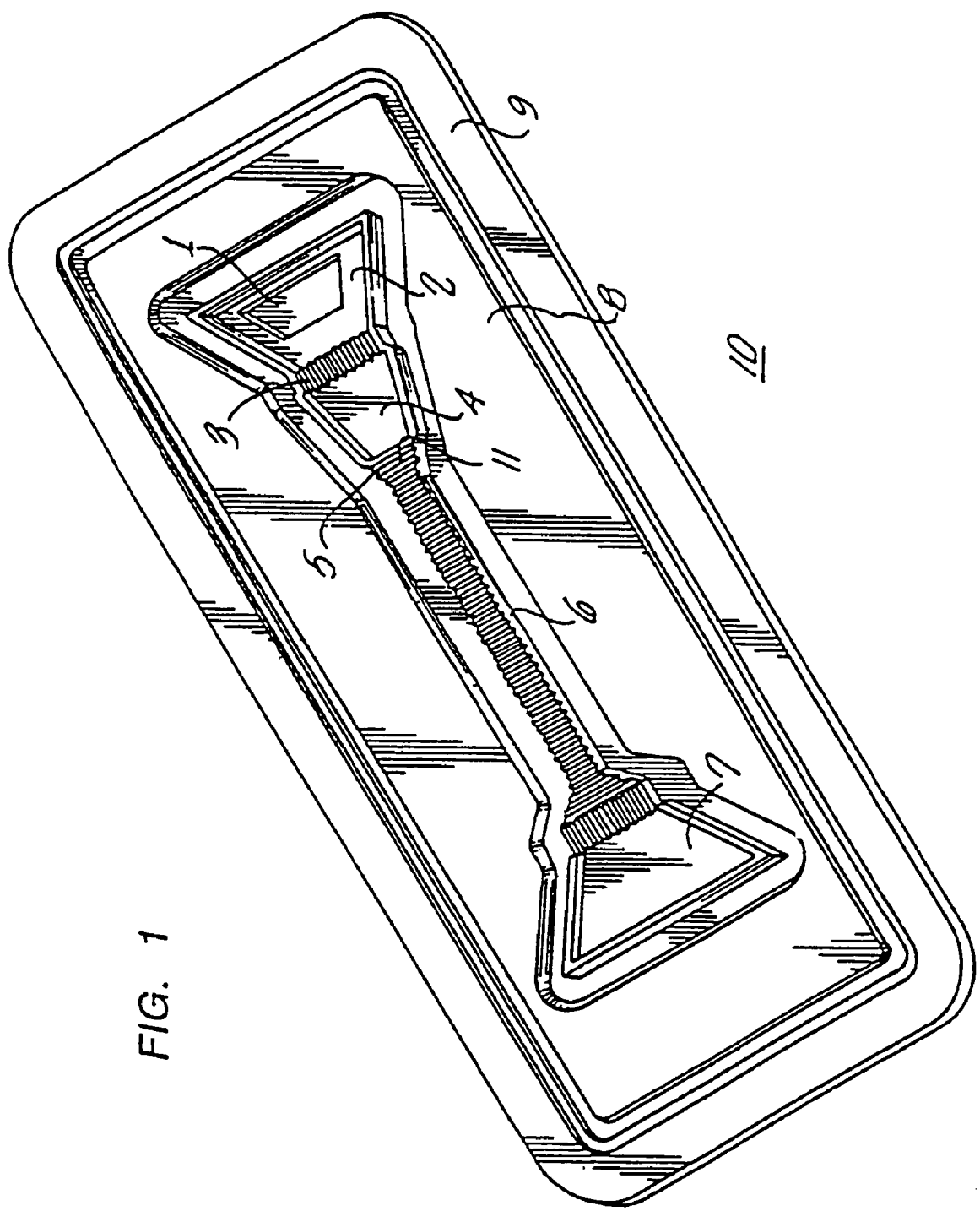
FIG. 1 is a partially schematic, top perspective view of a device in accordance with the present invention.

The inventive devices and methods of this invention overcome the problems found in the prior art providing devices and methods which do not require precise pipetting of sample, which do not use absorbent members, which include novel textures and elements for the controlled movement of reagents in the device and which are capable of providing quantitative assays.

The devices described herein do not use bibulous or porous materials, such as membranes and the like as substrates for the immobilization of reagents or to control the flow of the reagents through the device. A disadvantage of, for example, membranes in diagnostic devices is that on both microscopic and macroscopic scales the production of membranes is not easily reproducible. This can result in diagnostic devices which have differential properties of non-specific binding and flow characteristics. Membranes are very susceptible to non-specific binding which can raise the sensitivity limit of the assay. In one embodiment, the time gates of this invention can, however, be embedded in membranes or used in devices with membranes.

In the case of immunochromatographic assay formats such as those described in U.S. Pat. Nos. 4,879,215, 4,945,205 and 4,960,691, the use of membranes as the diagnostic element requires an even flow of reagents through the membrane. The problem of uneven flow of assay reagents in immunochromatographic assays has been addressed in U.S. Pat. Nos. 4,756,828, 4,757,004 and 4,883,688, incorporated herein by reference. These patents teach that modifying the longitudinal edge of the bibulous material controls the shape of the advancing front.

The devices of the current invention circumvent these membrane associated problems by the use of defined surfaces, including grooved surfaces, capillarity, time gates, novel capillary means, including channels and novel fluid flow control means alone or in various combinations, all of which are constructed from non-absorbent materials. In a preferred mode of this invention, the capillary channel of the diagnostic element is composed of grooves which are perpendicular to the flow of the assay reagents. The manufacture of grooved surfaces can be accomplished by injection molding and can be sufficiently reproducible to provide control of the flow of reagents through the device.

The assay devices, assay systems and device components of this invention can comprise two opposing surfaces disposed a capillary distance apart; at least one of the surfaces comprises the ability to detect at least one target ligand or a conjugate in an amount related to the presence or amount of target ligand in a sample. The inventive device components may be incorporated into conventional assay devices with membranes or may be used in the inventive membrane-less devices herein described and claimed. Components of the invention comprise flow control elements, measurement elements, time gates, elements for the elimination of pipetting steps, and generally, elements for the controlled flow, timing, delivery, incubation, separation, washing and other steps of the assay process.

Unlike assay devices of the prior art, the inventive assay devices described herein do not require the use of bibulous materials, such as papers or membranes. The inventive devices of the present invention rely on the use of defined surfaces, including grooved and textured surfaces, and capillarity alone or in various combinations to move the test reagents. The inventive devices described herein provide means for the controlled, timed movement of reagents within the device and do not require precise pipetting steps. The concepts and devices of the present invention are especially useful in the performance of immunoassays and nucleic acid assays of environmental and industrial fluids, such as water, and biological fluids and products, such as urine, blood, serum, plasma, spinal and amniotic fluids and the like.

Accordingly disclosed is an analytical device for determining the presence or amount of an analyte in a test sample. The device can comprise an array of structures, where one or more of said structures have a surface providing an immobilized ligand receptor covalently or non-covalently attached to said surface, and the immobilized ligand receptor capable of binding a target ligand. The device also comprises a plurality of channels wherein said test sample containing said analyte, analyte-analog, ancillary binding member, or labeled reagent flows through said channels, said analyte, analyte-analog, ancillary binding member, or labeled reagent diffusing across the width of said channels and binding to said immobilized reagent.

The device can comprise an inlet port and a vent; an array of structures, where each structure has a surface providing an immobilized receptor covalently or non-covalently attached to said surface of said structure, and capable of binding a ligand; a plurality of channels wherein said test sample containing a ligand, flows through said channels, said ligand diffuses across the width of said channels to bind said immobilized receptor; and, a labeled reagent comprising a specific binding member conjugated to a detectable label, where the detectable label is capable of producing a signal at said immobilized receptor which indicates the presence or amount of a ligand in a test sample.

Disclosed is an assay device comprising: a sample addition reservoir; a sample reaction barrier fluidly connected to said sample addition reservoir; a reaction chamber fluidly connected to said sample reaction barrier, said chamber having at least two fingers in the walls thereof, wherein said barrier has a higher capillarity than said reaction chamber; a time gate fluidly connected to the reaction chamber, said time gate capable of permitting fluid to pass therethrough at a desired flow rate; a diagnostic element fluidly connected to the time gate, said diagnostic element capable of immobilizing at least one conjugate in at least one zone; and, a used reagent reservoir fluidly connected to said diagnostic element, whereby fluid can flow in sequence from said reservoir, to said barrier, to said reaction chamber, to said time gate, to said diagnostic element then to said reservoir.

Disclosed is a device capable of performing an assay, said device comprising two or more surfaces that are in contact by fluid during performance of the assay, wherein a first device surface comprises a first immunoassay reagent immobilized thereon and a second capillary space surface comprises a second immunoassay reagent immobilized thereon.

Disclosed is a device capable of performing an assay, said device comprising a stop and an energy director. Accordingly during manufacture of this device, the energy director serves to seal a first device piece to a second device piece and to define a capillary space in the device, and the stop serves to allow preparation of a device chamber with uniform dimensions.

Disclosed is a zone comprising a region capable of having a fluid placed thereon, and a hydrophobic region adjacent to the region capable of containing a fluid placed thereon, whereby the hydrophobic region impedes the flow of fluid into that hydrophobic region. Also disclosed is an assay device comprising this zone. Also disclosed is a method to facilitate uniform drying of a liquid, where the method comprises: providing the zone; introducing liquid into the zone region capable of having a fluid placed thereon; and, and drying said liquid.

Devices in accordance with the invention were used to conduct assays on liquid samples suspected of containing an analyte of interest.

Disclosed is a surface configured to facilitate placement of a uniform layer of dried reagent thereon, said surface comprising a plurality of texture structures, whereby a plurality of menisci are formed when a fluid is placed in contact with the surface. Surfaces in accordance with the invention, and devices comprising such surfaces, were used to facilitate preparation of a uniform layer of a dried reagent on said surface.

Disclosed is a method of manufacturing analytical devices from a master. A master is provided that comprises device features in accordance with the invention, e.g., a master having an array of structures which have one or more channels therebetween. Thereafter, in accordance with manufacturing techniques known to those of ordinary skill in the art, copies of the master are made.

Disclosed is a method for manufacturing a capillary space comprising a hydrophobic surface and a hydrophilic surface. The method comprises applying a hydrophobic material to a hydrophilic surface that is capable of forming a lumenal surface of a capillary space; or, masking a region of a hydrophobic surface; applying a means for producing a hydrophilic surface of the surface whereby areas of the surface which are nonmasked become hydrophilic, and removing the masking to expose a hydrophobic region of a surface that is capable of forming a lumenal surface of a capillary space.

Disclosed is a capillary space that comprises a lumen comprising at least one rectilinear angle when viewed in a cross section, where the capillary also comprises a hydrophobic zone on a lumenal surface thereof. Also disclosed is a material configured to fit into a capillary space, said material comprising a hydrophobic zone on a surface thereof. Also disclosed is a material comprising a hydrophobic zone; where the zone, upon addition of liquid to the material, is capable of delimiting a discrete area of liquid on a surface on or within the material.

DEFINITIONS

In interpreting the claims and specification, the following terms shall have the meanings set forth below.

Target ligand—The binding partner to one or more receptors. Synonyms for target ligand are analyte, ligand or target analyte.

Ligand—Binding partner to one or more ligand receptor(s). A synonym for ligand is analyte. For example, a ligand can comprise an antigen, a nucleotide sequence, lectin or avidin.

Ligand Analogue—A chemical derivative of the target ligand which may be attached either covalently or noncovalently to other species, for example, to the signal development element. Ligand analogue and target ligand may be the same and both generally are capable of binding to the ligand receptor. Synonyms for ligand analogue are analyte analogue or target analyte analogue.

Ligand Analogue Conjugate—A conjugate of a ligand analogue and a signal development element. A ligand analogue conjugate can be referred to as a labeled ligand analogue.

Signal Development Phase—The phase containing the materials involving the signal development element to develop signal, e.g., an enzyme substrate solution.

Receptor—Chemical or biochemical species capable of reacting with or binding to target ligand, typically an antibody, a binding fragment, a complementary nucleotide sequence, carbohydrate, biotin or a chelate, but which may be a ligand if the assay is designed to detect a target ligand which is a receptor. Receptors may also include enzymes or chemical reagents that specifically react with the target ligand. A receptor can be referred to as a reagent or a binding member. A receptor which is neither a labeled receptor nor an immobilized receptor can be referred to as an ancillary receptor or an ancillary binding member. For example, a receptor can comprise an antibody.

Ligand Receptor Conjugate—A conjugate of a ligand receptor and a signal development element; synonyms for this term include binding member conjugate, reagent conjugate, labeled reagent or labeled binding member.

Signal Development Element—The element which directly or indirectly causes a visually or instrumentally detectable signal as a result of the assay process. Receptors and ligand analogues may be bound, either covalently or noncovalently to the signal development element to form a conjugate; when so bound these substances can be referred to as labeled. The element of the ligand analogue conjugate or the receptor conjugate which, in conjunction with the signal development phase, develops the detectable signal, e.g., an enzyme.

Reaction Mixture—The mixture of sample suspected of containing target ligand and the reagents for determining the presence or amount of target ligand in the sample, for example, the ligand analogue conjugate or the receptor conjugate. As used herein the reaction mixture may comprise a proteinaceous component which may be the target, a component of the sample or additive (e.g., serum albumin, gelatin, milk proteins).

Ligand Complement—A specialized ligand used in labeling ligand analogue conjugates, receptors, ligand analogue constructs or signal development elements.

Ligand Complement Receptor—A receptor for ligand complement.

Ligand Analogue-Ligand Complement Conjugate—A conjugate composed of a ligand analogue, a ligand complement and a signal development element.

Capture Efficiency—The binding efficiency of the component or components in the reaction mixture, such as the ligand analogue conjugate or the receptor conjugate, to the capture zone of the diagnostic element.

Capture Zone—The area on the diagnostic element which binds at least one component of the reaction mixture, such as the ligand analogue conjugate or the receptor conjugate.

Capillarity—The force induced by a capillary space, or the exhibition of capillary action. Capillarity can be affected by the solid surface or the liquid surface or both.

Biosensor—Any electrochemical, optical, electro-optical or acoustic/mechanical device which is used to measure the presence or amount of target ligands. For example, electrochemical biosensors utilize potentiometric and amperometric measurements, optical biosensors utilize absorbance, fluorescence, luminescence and evanescent waves. Acoustic/mechanical biosensors utilize piezoelectric crystal resonance, surface acoustic waves, field-effect transistors, chemical field-effect transistors and enzyme field-effect transistors. Biosensors can also detect changes in the physical properties of solutions in which receptor binding events take place. For example, biosensors may detect changes in the degree of agglutination of latex particles upon binding antigen or they may detect changes in the viscosity of solutions in response to receptor binding events.

DETAILED DESCRIPTION OF THE INVENTION

The present invention is directed to diagnostic testing devices for determining the presence or amount of at least one target ligand. FIG. 1 shows a preferred embodiment of a device 10 according to the invention. Generally, the devices of the invention have thicknesses of about 2 mm to 15 mm, lengths of about 3 cm to 10 cm and widths of about 1 cm to 4 cm. The dimensions may be adjusted depending on the particular purpose of the assay.

One device of this invention, as depicted in FIG. 1, generally illustrates some features of the inventive devices and portions of devices herein disclosed and claimed. The device 10 comprises various elements, a sample addition zone 1, a sample addition reservoir 2, a sample reaction barrier 3, a reaction chamber 4, a time gate 5, a diagnostic element 6, and a used reagent reservoir 7. The devices are comprised of capillary channels which are formed when a top member 8 is placed on the bottom member 9 a capillary distance apart and which move the reagents and sample throughout the device. The top and bottom members may be married, the various chambers sealed and the capillaries formed by a number of techniques, including but not limited to, gluing, welding by ultrasound, riveting and the like. The elements of the device can be used in various combinations with the diagnostic element 6 to achieve a variety of desired functions. As one skilled in the art will recognize these elements may be combined to perform one-step or multistep assays. The devices 10 may also be used in the formation of reaction mixtures for the assay process. The device 20 in FIG. 2 may be used to add pre-mixed reaction mixtures for the generation of signal which relates to the presence or amount of the target ligand.

Figure 1A:
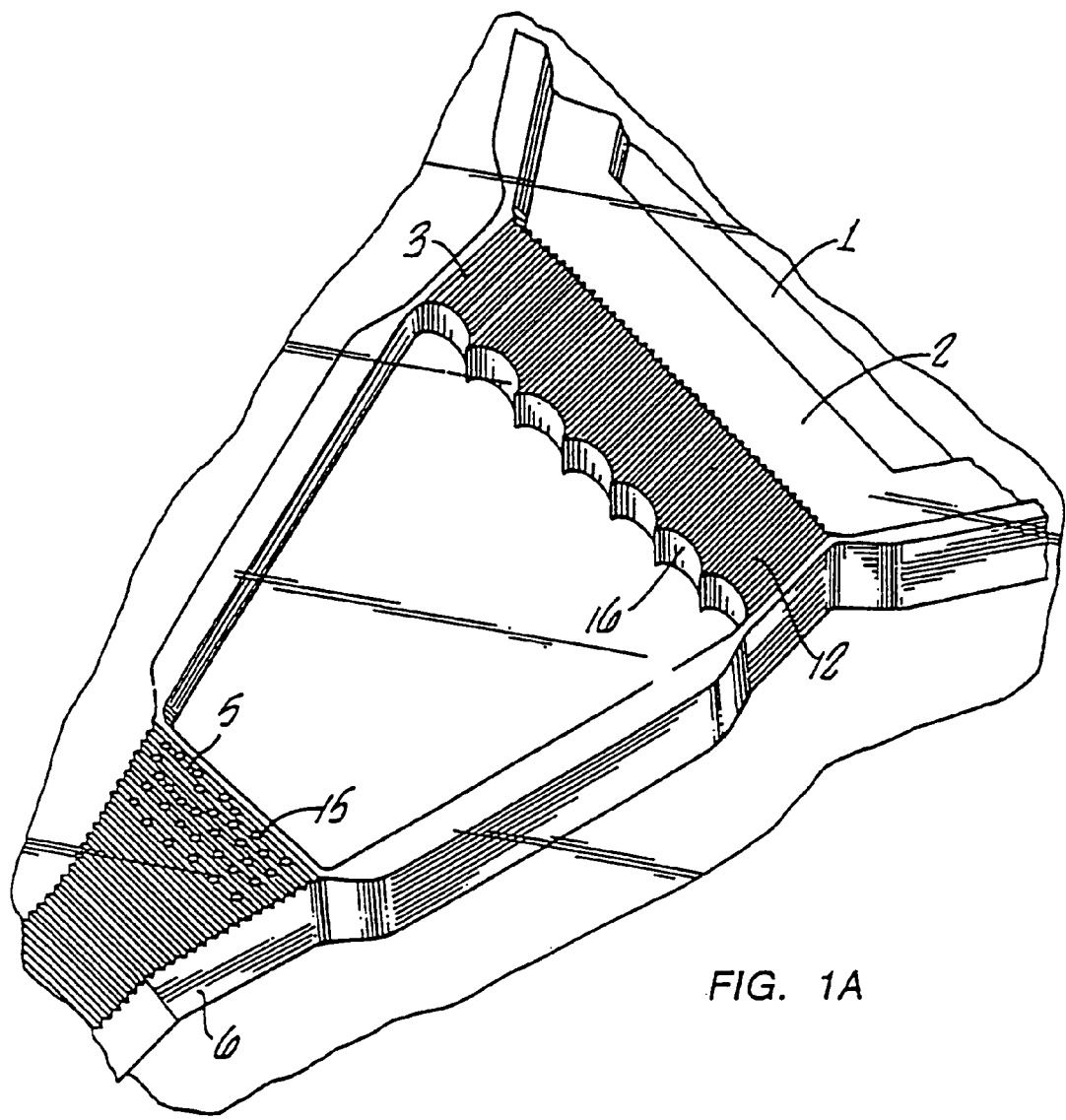
FIG. 1A is a partially schematic, perspective exploded view of the device showing the detail in the area of the sample addition reservoir, the sample-reaction barrier, the reaction chamber, the time gate and the beginning of the diagnostic element.
Figure 1B:
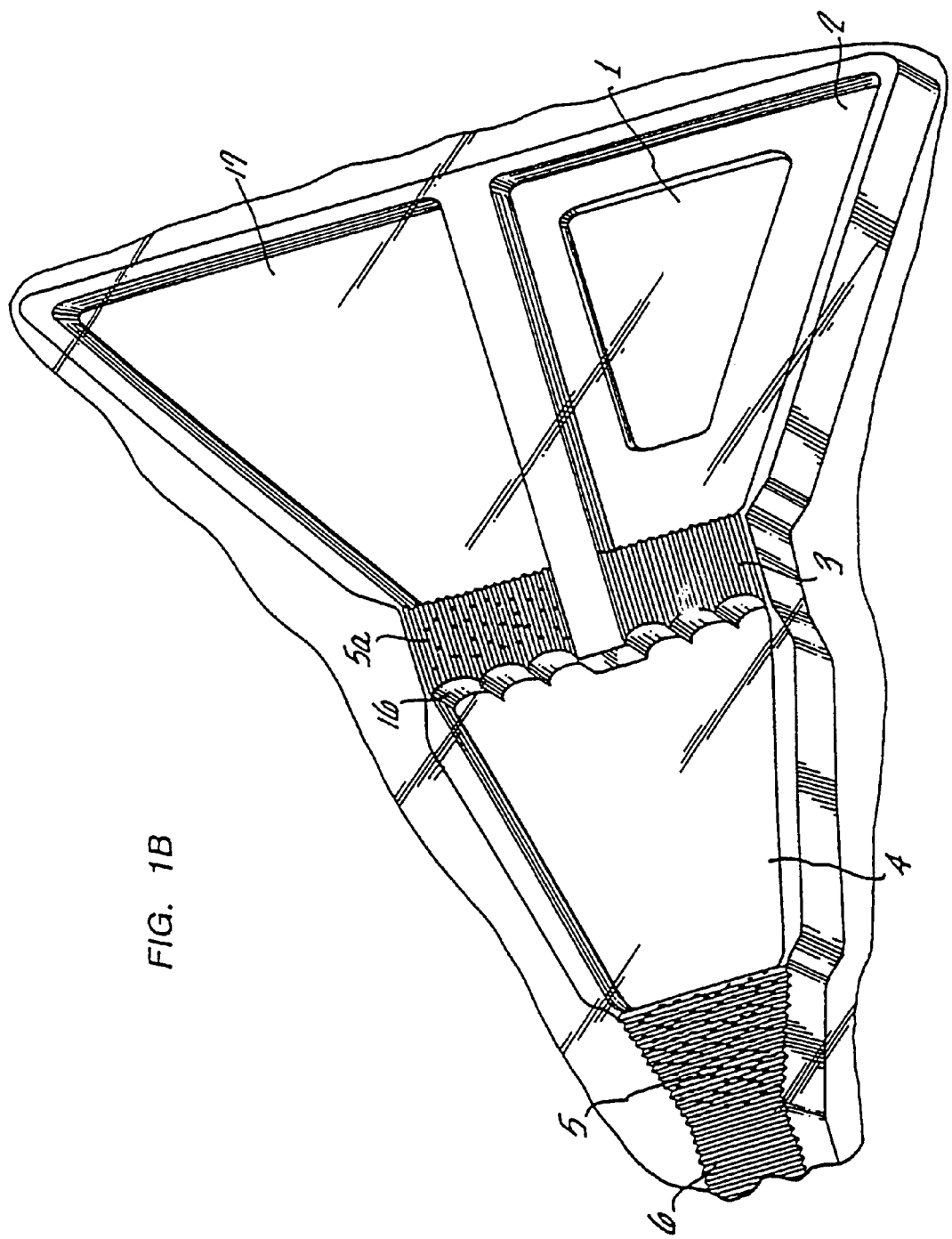
FIG. 1B is a partially schematic, perspective exploded view of the device showing the detail in the area of the optional reagent reservoir, the sample addition reservoir, the sample-reaction barrier, the reaction chamber, the time gate and the beginning of the diagnostic element.
Figure 1C:
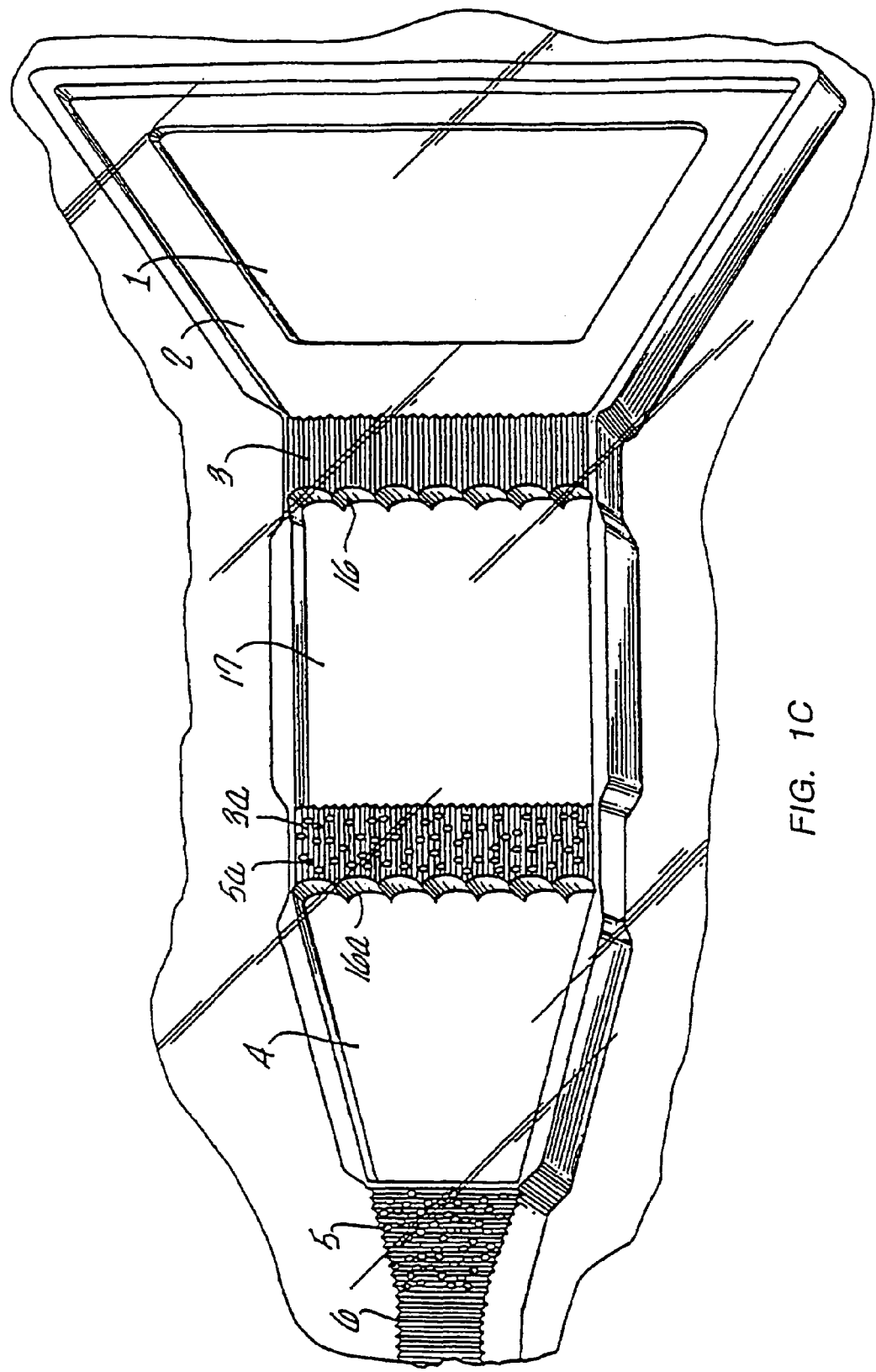
FIG. 1C is a partially schematic, perspective exploded view of the device showing the detail in the area of the optional reagent reservoir in fluid contact with the sample addition reservoir and the reaction chamber.
Figure 1D:
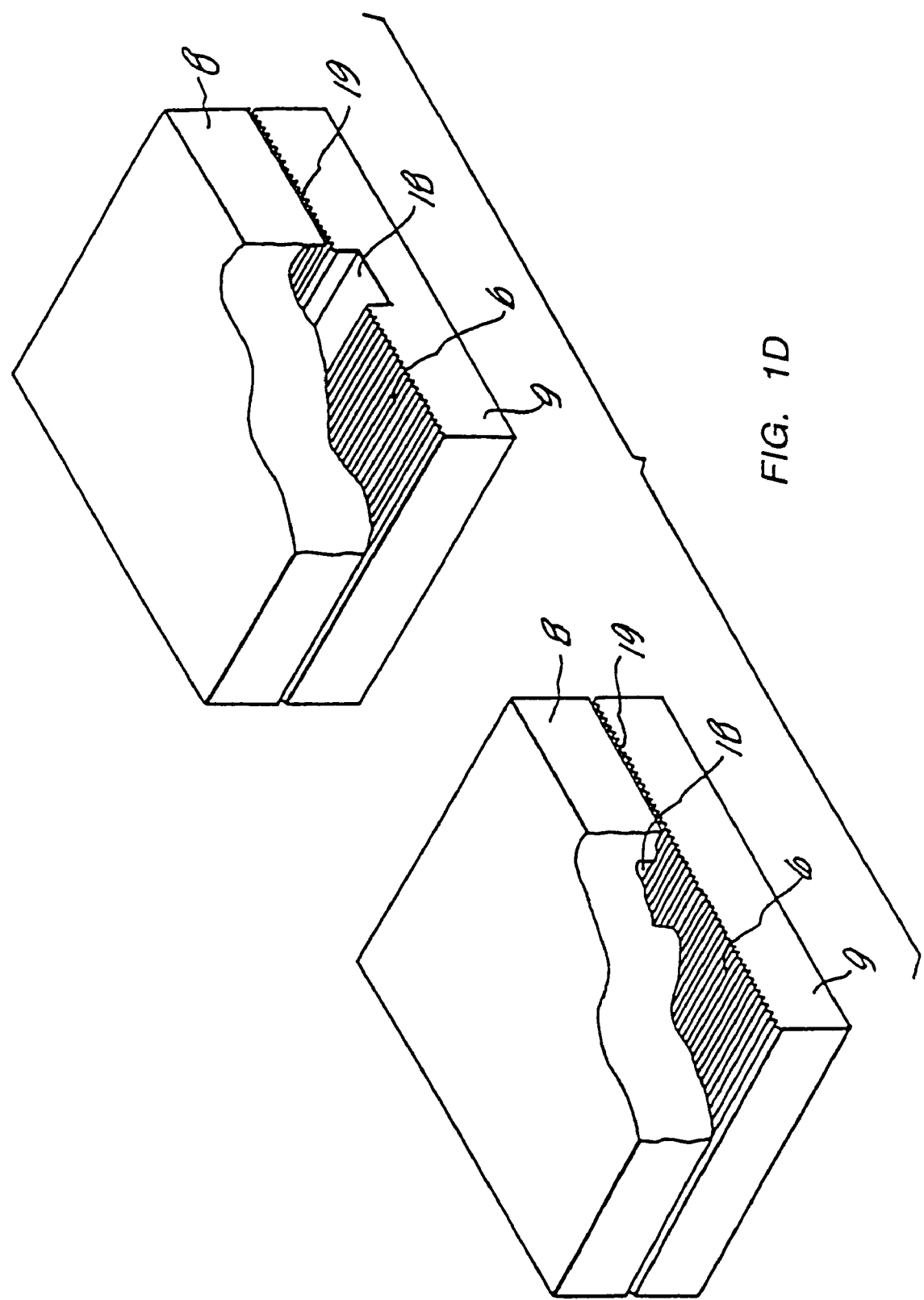
FIG. 1D is a partially schematic, perspective cutaway view of the flow control means.

An optional reagent chamber 17 may be incorporated into device 10 or 20 as depicted in FIG. 1B and FIG. 1C. The devices 10 and 20 may also be used with an optional fluid control means 18 as shown in FIG. 1D.

Features include, but are not limited to: 1) diagnostic elements which are not comprised of bibulous materials, such as membranes, 2) means to control the volume of sample or reaction mixture, 3) time gates, 4) novel capillary means, termed fingers herein and 5) novel flow control means, sometimes referred to as a "gap" herein and 6) used reagent reservoir which prevents backward flow of reagents. Those of skill in the art will appreciate that these elements are separately novel and nonobvious, and may be incorporated into diagnostic devices in various combinations and may be used with other elements known to those skilled in the art to achieve novel and nonobvious diagnostic test devices and heretofore unrealized benefits.

Components of the device (i.e., a physical structure of the device whether or not a discrete piece from other parts of the device) can be prepared from copolymers, blends, laminates, metallized foils, metallized films or metals. Alternatively, device components can be prepared from copolymers, blends, laminates, metallized foils, metallized films or metals deposited one of the following materials: polyolefins, polyesters, styrene containing polymers, polycarbonate, acrylic polymers, chlorine containing polymers, acetal homopolymers and copolymers, cellulosics and their esters, cellulose nitrate, fluorine containing polymers, polyamides, polyimides, polymethylmethacrylates, sulfur containing polymers, polyurethanes, silicon containing polymers, glass, and ceramic materials.

Alternatively, components of the device are made with a plastic, elastomer, latex, silicon chip, or metal; the elastomer can comprise polyethylene, polypropylene, polystyrene, polyacrylates, silicon elastomers, or latex.

Alternatively, components of the device can be prepared from latex, polystyrene latex or hydrophobic polymers; the hydrophobic polymer can comprise polypropylene, polyethylene, or polyester.

Alternatively, components of the device can comprise TEFLON®, polystyrene, polyacrylate, or polycarbonate.

Alternatively, device components are made from plastics which are capable of being milled or injection molded or from surfaces of copper, silver and gold films upon which are adsorbed various long chain alkanethiols. The structures of plastic which are capable of being milled or injection molded can comprises a polystyrene, a polycarbonate, or a polyacrylate.

Each of the elements of devices 10 and 20 will be described separately, then representative descriptions of the devices of this invention will follow.

Sample Addition Zone

Figure 2:
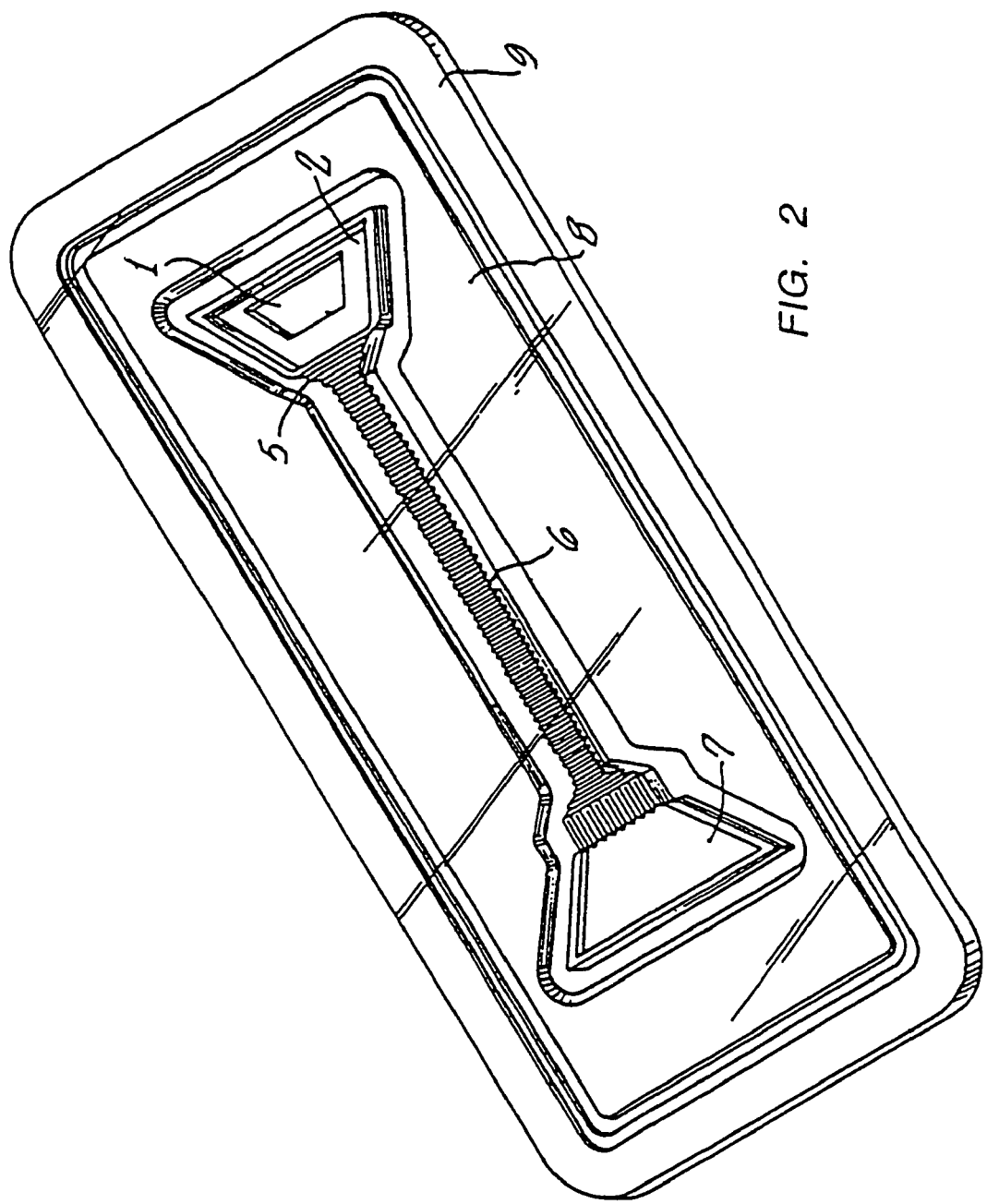
FIG. 2 is a partially schematic, perspective view of a second device in accordance with this present invention, which may be used to add pre-mixed reaction mixtures.

Referring to FIGS. 1 and 2, the sample addition zone 1 of the devices 10 and 20 is the area where sample is introduced to the device. The sample addition zone 1 can be a port of various configurations, that is, round, oblong, square and the like or the zone can be a trough in the device.

Sample Addition Reservoir

Referring to FIGS. 1 and 2, the sample addition reservoir 2 is an element of the device which receives the sample. Referring now to FIG. 1, the volume of the sample addition reservoir 2 should be at least the volume of the reaction chamber 4 or greater. The sample addition reservoir 2 can be a capillary space or it can be an open trough. In addition, a filter element can be placed in or on the sample addition reservoir 2 to filter particulates from the sample or to filter blood cells from blood so that plasma can further travel through the device. The sample addition reservoir can comprise a vent (not illustrated) to facilitate escape of gas and liquid filling of the reservoir.

In a preferred embodiment, the volume or capacity of the sample addition reservoir 2 is 1 to 5 times the volume of the reaction chamber 4. In general, one selects a volume or capacity of this reservoir 2 such that if the excess sample is used to wash the diagnostic element 6 then enough volume of sample is needed to thoroughly remove any unbound reagents from the diagnostic element 6 arising from the assay process.

Reservoir 2 may also contain certain dried reagents which are used in the assay process. For example, a surfactant can be dried in this reservoir 2 which dissolves when sample is added. The surfactant in the sample would aid in the movement of the sample and reaction mixture through the device by lowering the surface tension of the liquid. The sample addition reservoir 2 is generally in direct fluid contact with the sample-reaction barrier 3 (FIG. 1) or the diagnostic element 6 (FIG. 2).

Sample-Reaction Barrier

As depicted in FIG. 1, the sample-reaction barrier 3 separates the sample in the sample addition reservoir 2 from the reaction mixture in the reaction chamber 4. The sample-reaction barrier is desired because it provides the device with the capability of forming a precise reaction mixture volume. A precise volume of the reaction mixture is generally necessary for assays in which semi-quantitative or quantitative results are desired. Thus, a precise pipetting step of the sample to the device is not required because the sample reaction barrier forms a reaction chamber of precise volume into which the sample is capable of flowing. The sample reaction barrier 3 is desired because the reactions which take place in the reaction chamber 4 should preferably be separated from the excess sample in the sample addition reservoir 2.

The sample reaction barrier 3 comprises a narrow capillary, generally ranging from about 0.01 mm to 0.2 mm and the surfaces of the capillary can be smooth or have a single groove or a series of grooves which are parallel or perpendicular to the flow of sample. In a preferred embodiment of the sample reaction barrier 3, now referring to FIG. 1A, grooves 12, parallel to the flow of sample, are incorporated onto one surface of the device a capillary distance, for example, 0.02 mm to 0.1 mm, from the other surface. The volume of sample which fills the sample-reaction barrier 3 (FIG. 1A) should be kept to a minimum, from about 0.01% to 10% of the reaction chamber 4 volume so that the reagents of the reaction chamber 4 do not significantly diffuse back into the sample in the sample addition reservoir 2. That is, the diffusion of the reaction mixture back into the excess sample should be kept to a minimum so that the chemical or biochemical reactions occurring in the reaction mixture are not substantially influenced by the excess sample in the sample addition reservoir 2. Groove depths can range from about 0.01 mm to 0.5 mm and preferably from about 0.05 mm to 0.2 mm. When more than one groove is used for this element, the number of grooves in this element is typically between 10 and 500 grooves per cm and preferably from about 20 to 200 grooves per cm. Sample from the sample addition reservoir 2 flows over the grooves 12 by capillary action and then into the reaction chamber 4. In a further preferred embodiment, grooves, hereafter termed "fingers" 16, are situated in the wall of the reaction chamber 4 in fluid contact with the grooves 12 or capillary space of the sample-reaction barrier 3. These fingers 16 are typically 0.5 mm to 2 mm wide, preferably 1 mm to 1.5 mm wide and typically 0.1 mm to 1.5 mm in depth, preferably about 0.2 to 1 mm in depth. The fingers 16 in the wall of the reaction chamber 4 aid in the capillary flow of the sample into the reaction chamber 4. That is, the fingers allow fluid to move from a capillary where the capillarity is relatively high to a capillary where the capillarity is lower. Thus, the capillary at the sample-reaction barrier is generally more narrow and has a greater capillarity than the capillary or space of the reaction chamber. This difference in capillarity can cause the flow of sample or fluid in the device to stop in the sample-reaction barrier capillary. Presumably, the fingers break the surface tension of the fluid at the interface of the two capillaries or spaces and thereby cause the fluid to move into a capillary or space of lower capillarity. One can appreciate that the utility of fingers can be extended to any part of the device where fluid must flow from high capillarity to low capillarity. In practice, this is usually when the direction of fluid flow is from a narrow capillary (higher capillarity) to a wider capillary (lower capillarity).

The top surface of the sample reaction barrier may also be used to immobilize reagents used in the assay process such that the sample flows over the sample reaction barrier, dissolves the reagents and moves into the reaction chamber. The movement of the sample and reagents into the reaction chamber may act as a mixing means.

Reaction Chamber

Referring to FIG. 1, the sample moves into the reaction chamber 4 from the sample-reaction barrier 3. The reagents of the device 10 are preferably placed in the reaction chamber 4, for example, as dried or lyophilized powders, such that when the sample enters the reaction chamber 4 the reagents quickly reconstitute. The volume of the reaction chamber 4 is the volume of sample which defines the reaction mixture. The reaction chamber may be sealed on two sides, for example, by ultrasonic welding of the top and bottom members. Thus, delivery of the sample to the device 10 at the sample addition zone 1 does not require a precise pipetting step to define the volume of the reaction mixture. Mixing features which mix the reaction mixture can also be incorporated in conjunction with the reaction chamber element 4, such as those described in U.S. Pat. Appl. Ser. No. 711,621 filed Jun. 5, 1991, now abandoned, hereby incorporated by reference. The sample fills the reaction chamber 4 because of capillary forces and also, potentially, because of the hydrostatic pressure exerted by the sample in the sample addition reservoir 2.

A surface of reaction chamber 4 may be smooth or comprised of texture structures such as posts or grooves. Texture on a device surface can facilitate drying of reagents on the surface during preparation of the device, and can facilitate movement of sample into the reaction chamber 4. Texture on a device surface facilitates uniform placement of dried reagents on the surface as follows: A liquid reagent-containing fluid is placed in contact with the textured surface, and small reagent fluid menisci form adjacent each texture structure. Absent the presence of texture, the fluid would tend to form larger menisci at corners of the entire chamber, which when dried would produce a non-uniform layer of dried reagent. When texture structures are designed into the device, the presence of numerous small menisci leads to a more uniform layer of reagent that is dried throughout the chamber.

The volume of the reaction chamber 4, and thereby the reaction mixture, may be any volume which accommodates the reagents and which provides the desired sensitivity of the assay. The shape of the reaction chamber 4 should be such that the movement of the reaction mixture from the reaction chamber 4 is not turbulent and eddies are not formed as a result of the movement out of the reaction chamber 4. A preferred shape of the reaction chamber 4 is shown in FIG. 1. The depth of the reaction chamber 4 should be commensurate with the width of the chamber to accommodate the desired reaction mixture volume. The depth of the reaction chamber can range from about 0.05 mm to 10 mm and preferably from 0.1 mm to 0.6 mm. To accommodate a particular volume of the reaction chamber, the length and width of the reaction chamber should be adjusted and the depth maintained as narrow as is practical. The reaction chamber 4 is in direct fluid contact with the sample-reaction barrier 3 and the diagnostic element 6 or time gate 5. In addition, the reaction chamber 4 may also be in direct fluid contact with an optional reagent reservoir 17 as shown in FIGS. 1B and 1C.

A preferred embodiment of the reaction chamber utilizes a ramp which extends from the bottom of the reaction chamber to the surface of the diagnostic element. The ramp minimizes or prevents mixing and eddy formation of the reaction mixture with the sample at the interface of the reaction chamber and the diagnostic element as the fluid moves through the device. Thus, the ramp allows a smooth transition of the fluid out of the reaction chamber and onto the diagnostic element. The length of the ramp should be optimized for each depth of the reaction chamber, but generally, the ramp is at an angle of between 25 and 45 degrees relative to the floor of the reaction chamber.

Time Gate

Referring to FIG. 11A, the time gate 5 holds the reaction mixture in the reaction chamber 4 for a given period of time. The concept of the time gate is that a predominantly aqueous solution cannot pass through a sufficiently hydrophobic zone until the hydrophobic zone is made sufficiently hydrophilic. Furthermore, the hydrophobic zone is made hydrophilic through the binding of a component in the aqueous solution to the hydrophobic zone. The sufficiently hydrophobic zone is generally in a capillary space. The driving force for fluid movement over or through the time gate may be either the capillarity of the space or hydrostatic pressure exerted by the sample or a combination of both of these forces. The amount of time which is required to hold the reaction mixture in the reaction chamber 4 is relative to the assay process such that the reactions which occur in the reaction chamber 4 as a result of the assay process will reflect the presence or amount of target ligand in the sample. Thus, the time gate 5 delays the flow of the reaction mixture onto the diagnostic element 6. The time gate 5 delays the flow of the reaction mixture by the principle that a hydrophilic liquid, such as an aqueous solution or one which has a dielectric constant of at least 40, cannot move past a sufficiently hydrophobic barrier in a capillary channel. In designing and building a time gate, one can begin with a hydrophobic surface, such as are found on native plastics and elastomers (polyethylene, polypropylene, polystyrene, polyacrylates, silicon elastomers and the like) or silicon chip surfaces or metal surfaces, either smooth, grooved or textured and a capillary is formed by an opposing surface which can be hydrophobic or hydrophilic in nature and smooth, grooved or textured. The hydrophobic surface(s) in the capillary have a microscopic surface area onto which can bind components which are generally soluble in a predominantly aqueous solution. The hydrophilic character and the concentration of the component(s) in the reaction mixture and the overall surface area of the time gate affects the mechanics of the time gate. The amount of time for which the time gate 5 holds the reaction mixture is related to the rate of binding of a component(s) from the reaction mixture to the hydrophobic barrier. The binding of the component(s) from the reaction mixture changes the hydrophobic barrier to a zone which is sufficiently hydrophilic over which or through which the reaction mixture can flow. Creating the sufficiently hydrophilic surface then allows the fluid to flow as if the time gate had not been in the device. Thus, fluid flow through the remainder of the device is not affected once the time gate has been made hydrophilic. Other devices described which incorporate fluid delay means, for example, in U.S. Pat. Nos. 4,426,451 and 4,963,498, hereby incorporated by reference, only require an external manipulation of the device to start fluid flow or utilize capillary constrictions to slow fluid flow. In this latter case, the capillary constriction used to delay fluid flow will affect the fluid flow through the remainder of the device.

In a preferred embodiment, for example, the time gate 5 can be composed of latex particles 15 (FIG. 1A, not drawn to scale), such as polystyrene latexes with diameters of between about 0.01 μm and 10 μm or hydrophobic polymers, such as polypropylene, polyethylene, polyesters and the like, which are introduced onto the device in the appropriate zone where the reaction mixture must travel. In another preferred embodiment, the time gate can be created by application of a hydrophobic chemical, such as an ink or a long chain fatty acid, or a hydrophobic decal to the desired zone. The hydrophobic chemical or decal is generally not soluble or is poorly soluble in the reaction mixture. In yet another preferred embodiment, the time gate can also be formed by changing a hydrophilic surface to a hydrophobic surface. For example, hydrophobic surfaces made hydrophilic by plasma treatment can be converted back to a hydrophobic surface by the application of solvents, ultraviolet light or heat and the like. These treatments can act to change the molecular structure of the hydrophilic, plasma modified surface back to a hydrophobic form.

The component(s) in the reaction mixture which bind to the hydrophobic zone may be various proteins, polypeptides, polymers or detergents. A preferred protein is bovine serum albumin. The time delay provided by the time gate 5 depends on the concentration of the component(s) in the reaction mixture, for example, bovine serum albumin, which binds to the hydrophobic zone, for example, the surface area provided by the latex particles 15. Another preferred embodiment of the time gate 5 utilizes polyelectrolytes which are hydrophobic and which become hydrophilic by exposure to the buffering capacity of the reaction mixture. The time gate 5 would be comprised of, for example, polyacrylic acid, which in its protonated form it is hydrophobic. The reaction mixture, if buffered above the $pK_a$ of the polyacrylic acid, would deprotonate the acid groups and form the hydrophilic salt of the polymer. In this case, the time delay is related to the mass of polyelectrolyte and the pH and the buffering capacity of the reaction mixture.

The geometry or shape of the time gate can influence the area of the time gate that the fluid will pass over or through. That is, the time gate can be designed to direct the flow of liquid through a specific area of the time gate. By directing the fluid to flow through a defined area of the time gate the reproducibility of the time delay is improved. FIG. 6 shows representative geometries of time gates. For example, as shown in FIG. 6, time gates a-d, the time gates have V-shapes incorporated into their design, and more specifically, the length of the time gate (defined as the distance the fluid must cross over or through in order to pass the time gate) is less at the tip of the V than in the body of the time gate. Thus, in a preferred mode, the fluid will cross over or pass through the time gate where the length is shortest thereby directing fluid flow through the time gate in a consistent manner. In general, the directionality of fluid flow over or through the time gates is represented by opposing arrows in FIG. 6. In a preferred embodiment, the orientation of the time gates b, c and d of FIG. 6 are such that the fluid touches the flat portion of the time gate first rather than the V shape. In other words, the preferred direction of flow for the time gates b, c and d of FIG. 6 is represented by the up arrow. In cases where the time gate is simply a line, for example as seen in FIG. 6, time gate e and f, the path of fluid flow over or through the time gate can occur at any point on the time gate. Thus, the time gates which have geometries directing the fluid flow over or through a consistent area of the time gate are preferred. For example, time gates with lengths ranging from about 1.3 mm to 0.13 mm achieve delay times of approximately 0.3 min to 5.5 min, respectively, when the distance between surfaces is about 0.018 mm. When the time gate is V-shaped, the length of the time gate 4 at the tip of the V has dimensions smaller than the length of the time gate at the remaining portion of the V; that is, the arms of the V should have a length roughly 2 to 5 times the length of the V tip, as for example, FIG. 7, time gate a, illustrates. FIG. 7, time gate b, shows that only a small area of the time gate is crossed over or through at the tip of the V as compared with the remainder of the time gate. The time gate should span the width of the capillary or space so that the entire fluid front comes in contact with the time gate. If the time gate was not as wide as, for example, the diagnostic element, then the fluid front would go around the time gate. Thus, the time gate should "seal" the fluid in the space during the delay period.

Referring to FIG. 1, one skilled in the art can recognize that each device 10 could incorporate one or more time gates to achieve the desired function of the device. FIG. 8 shows some examples of the sequential placement of several time gates of FIG. 6. For example, as discussed in the next section, Optional Reagent Chambers, if a sequential addition immunoassay was to be performed by the device then two time gates would allow two sequential incubation steps to be performed by the device prior to the movement of the reaction mixture to the diagnostic element. In another example, if an incubation of the reaction mixture on the capture zone or zones of the diagnostic element(s) 6 was required then a time gate(s) would be placed immediately behind the capture zone or zones. This use of the time gate may arise in cases where poor efficiency of binding of the component in the reaction mixture to the capture zone of the diagnostic element would prevail.

Another application of the time gate involves the placement of a time gate on a surface which is not part of a capillary space. For example, the time gate can be placed on a hydrophilic surface, which alone without a capillary space will allow liquids to move. This is generally the case when a substantial volume of liquid is placed on a surface and it spreads because of surface tension and because of the hydrostatic pressure of the liquid pushing the meniscus outwardly. The time gate then would function to delay the advance of the fluid front because the hydrostatic nature of the surface of the time gate would stop the movement of liquid. As the meniscus of the advancing liquid touches the time gate, the component or components in the liquid binds to the time gate to create a sufficiently hydrophilic surface for a continued advance of the liquid on the surface.

Yet another embodiment of the time gate involves the positioning of a time gate prior to a membrane which is used to capture a conjugate or receptor. In yet another embodiment of the time gate, the time gate can be composed of hydrophobic surfaces in a membrane. In those cases, the hydrophobic membrane is positioned prior to the portion of membrane which captures the conjugate or receptor and may be positioned after a reaction chamber or a portion of membrane where reagents of the assay are placed or embedded and where the reagents incubate for a defined period of time. The time gate in the membrane can be formed by application of raw latex particles in the membrane at an appropriate solids concentration ranging from about 0.01% to 10%. The size of the latex particles should be slightly less than the pore size of the membrane so that the latex becomes imbedded within the membrane. The density of latex within the membrane at the time gate should be uniform so that the reaction mixture does not circumvent the time gate. For example, the latex size used to create a time gate for a membrane with a pore size of 1 μm can range between 0.05 and 0.2 μm. Since the distribution of pore sizes in membranes varies widely, the actual size of latex used must be arrived at by experimentation. The hydrophobic nature of the membrane used for the time gate can also be formed by plasma treatment or by treatment of the membrane with hydrophobic chemicals or polymers that adsorb to the membrane. One skilled in the art can appreciate that the teachings described herein of the inventive features of the time gate can be utilized to design time gates in a variety of diagnostic devices which utilize membranes. That is, devices described, for example, in U.S. Pat. Nos. 4,435,504, 4,727, 019, 4,857,453, 4,877,586 and 4,916,056, hereby incorporated by reference, can incorporate a time gate, for example, prior to the membrane or in the membrane which captures the conjugate or receptor.

Optional Reagent Chambers

Referring to FIGS. 1B and 1C, the optional reagent chamber 17 is useful for the introduction of reagents into the assay process. In general, the optional reagent chamber 17 may be in direct fluid contact with the sample addition reservoir 2 via a sample reaction barrier 3 or a port the reaction chamber 4 or the diagnostic element 6, via a sample reaction barrier 3 or a port. For example, FIG. 1B shows the optional reagent chamber 17 in direct fluid contact with the reaction chamber 4. The flow of the introduced reagent may be controlled by a time gate 5a and fingers 16 can aid in the movement of reagents into the reaction chamber 4. Referring now to FIG. 1C, for example, if a sequential addition immunoassay was to be performed by the device then 2 time gates 5 and 5a would and fingers 16 can aid in the movement of reagents into the reaction chamber 4. Referring now to FIG. 1C, for example, if a sequential addition immunoassay was to be performed by the device then 2 time gates 5 and 5a would allow 2 sequential incubation steps to be performed in the optional reagent chamber 17 and then in the reaction chamber 4 by the device prior to the movement of the reaction mixture onto the diagnostic element 6. That is, sample would be applied to the sample addition reservoir 2 through the sample addition zone 1 and the sample flows over the sample reaction barrier 3 and into the optional reagent chamber 17 by the aid of fingers 16 where the first set of reactions would occur. The time gate 5a, after the appropriate amount of time, would allow the reagents to flow over the sample reaction barrier 3a and into the reaction chamber 4 by the aid of fingers 16a where the next set of reactions would take place. After the appropriate amount of time, the time gate 5 allows the flow of reaction mixture onto the diagnostic element 6.

Fluid Control Means

Referring to FIG. 1D, the optional fluid control means 18 is designed to control the flow of the reaction mixture in the device. More specifically, the optional fluid control means 18 causes the volume of the reaction mixture to flow over the capture zone of the diagnostic element 6 at a rate which allows for an optimum capture of reagents onto the capture zone. After the volume of the reaction mixture flows over the capture zone the rate of flow of the excess reagents may be increased. The differential rate of flow of the reagents in the device is achieved by designing a gap 18 between the surfaces of the capillary space 19 of the diagnostic element 6. The size of the gap 18 is larger than the capillary space 19 of the diagnostic element 6. The gap 18 generally follows the capture zone or the zone where the rate of flow is required to be decreased. The gap 18 in the diagnostic element 6 thus has an associated volume. The volume of the gap 18 is filled with the reaction mixture by capillary action as it moves through the device. Since the gap 18 after the capture zone is greater than the capillary space 19 of the diagnostic element 6 a drop in capillary pressure at the beginning of the gap 18 results in a decrease in the rate of flow of the reaction mixture into the gap 18 and therefore a decrease in the rate of flow of the reaction mixture over the capture zone. Varying the size of the gap 18 changes the capillarity in the gap and thus the flow of the reaction mixture over the capture zone. In the case of immunoassays requiring a wash step to remove unbound reagents from the diagnostic element 6, it is generally desired that the rate of flow of the wash solution over the diagnostic element 6 is faster than the rate of flow of the reaction mixture over the diagnostic element 6 because this decreases the time of the assay. The shape of the gap can take many forms. As shown in FIG. 1D, the gap has square corners, however, the gap can be shaped as a trapezoid or triangle which would change the rate of flow of the reaction mixture while flowing into the gap. One skilled in the art can also appreciate that for certain immunoassays a wash step is not required.

The control of the rate of flow of the reagents in the device can also be used to allow chemical reactions to take place in one zone of the device before the reagents move to another area of the device where the extent of reaction of the reagents is monitored or where further reaction may take place. For example, several fluid control means could be incorporated into a device for use in immunoassays where a sequential addition and incubation of reagents is necessary. That is, the sample comes in contact with the first reagents and the time for the reaction of the sample and first reagents is controlled by a first gap. When the first gap is filled with fluid, the reaction mixture continues to the second reagents at which time an additional chemical reaction can subsequently take place. The time required for completion of this second reaction can also be controlled by a second gap before further flow of the reaction mixture along the diagnostic element. Chemical and biochemical reactions also take place in the volume of the gap, for example, by immobilizing reagents in the gap.

Diagnostic Element Referring to FIGS. 1 and 2, the diagnostic element 6 is formed by opposing surfaces which are a capillary distance apart through which the reaction mixture flows and on which are placed one or more capture zones. The capture zones are comprised of reagents, such as receptors, or devices, such as biosensors which bind or react with one or more components from the reaction mixture. The binding of the reagents from the reaction mixture to the capture zones of the diagnostic element 6 is related to the presence or amount of target ligand in the sample. One or more receptors or biosensors can be placed on the diagnostic element 6 to measure the presence or amount of one or more target ligands. The receptors or biosensors can be placed in discrete zones on the diagnostic element 6 or they can be distributed homogeneously or heterogeneously over the surface. Receptors or other chemical reagents, for example, a receptor against the signal generator can also be immobilized on the diagnostic element 6 to verify to the user that the reagents of the reaction mixture are viable and that the reaction mixture passed through the zones of the receptors or biosensors. A single receptor or biosensor can be placed over the majority of the diagnostic element 6 such that as the reaction mixture flows through the diagnostic element 6 the components from the reaction mixture bind to the surface of the diagnostic element 6 in a chromatographic fashion. Thus, the distance which the component of the reaction mixture binds would be related to the concentration of the target ligand in the sample. The reagents, such as receptors, are immobilized on the surface of the diagnostic element 6 through covalent bonds or through adsorption. A preferred embodiment is to immobilize receptor coated latex particles, for example of diameters ranging from about 0.1 µm to 5 µm. In addition, particles termed "nanoparticles" can also be coated with receptor and the resulting nanoparticles can be immobilized to the diagnostic element through adsorption or covalent bonds. Nanoparticles are generally composed of silica, zirconia, alumina, titania, ceria, metal sols, and polystyrene and the like and the particle sizes range from about 1 nm to 100 nm. The benefit of using nanoparticles is that the surface area of the protein coating the nanoparticle as a function of the solids content is dramatically enhanced relative to larger latex particles. The surfaces of the diagnostic element 6 would allow the receptor coated nanoparticles or latex particles to bind to the diagnostic element 6. In a preferred embodiment, the receptors bind to the surface of the diagnostic element through electrostatic, hydrogen bonding and/or hydrophobic interactions. Electrostatic, hydrogen bonding and hydrophobic interactions are discussed, for example, in Biochemistry 20, 3096 (1981) and Biochemistry 29, 7133 (1990). For example, the diagnostic element 6 can be treated with a plasma to generate carboxylic acid groups on the surface. The receptor coated latex particles are preferably applied to the diagnostic element 6 in a low salt solution, for example, 1-20 mM, and at a pH which is below the isoelectric point of the receptor. Thus, the negative character of the carboxylic acid groups on the diagnostic element 6 and the positive charge character of the receptor latex will result in enhanced electrostatic stabilization of the latex on the diagnostic element 6. Hydrogen bonding and hydrophobic interactions would also presumably contribute to the stabilization and binding of the receptor latex to the diagnostic element 6. Magnetic fields may also be used to immobilize particles which are attracted by the magnetic field.

Figure 5:
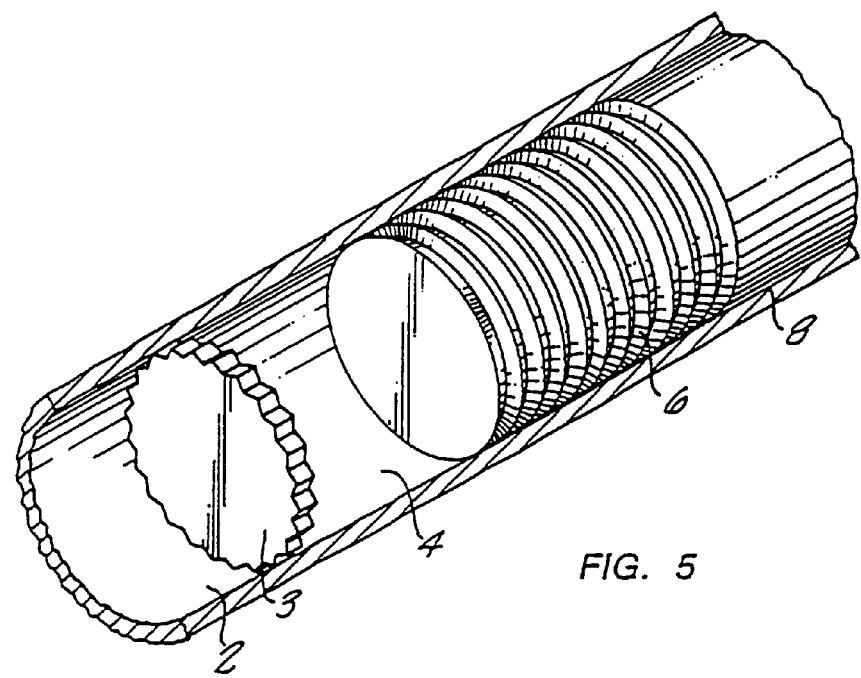
FIG. 5 is a partially schematic view of embodiments of these devices which are columnar or have curved opposing surfaces.
Figure 6A:
FIG. 6 is a top view of time gates.
Figure 6B:
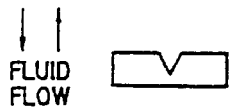
Figure 6C:
Figure 6D:
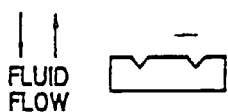
Figure 6E:
Figure 6F:
Figure 7A:
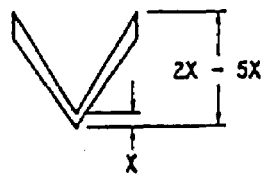
FIG. 7 shows typical dimensions for a preferred time gate.
Figure 7B:
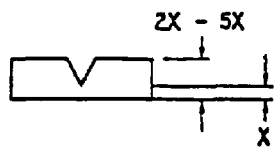
Figure 7C:
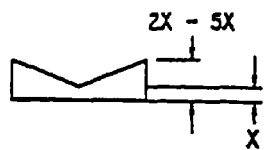
Figure 7D:
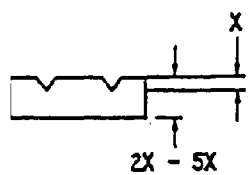
Figure 7E:
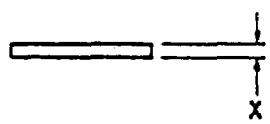
Figure 7F:
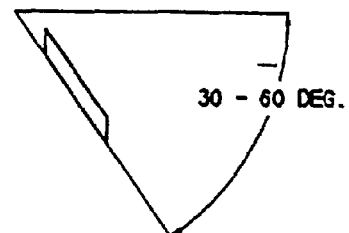
Figure 8A:
FIG. 8 is a top view of sequential time gates.
Figure 8B:
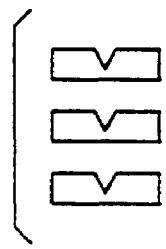
Figure 8C:
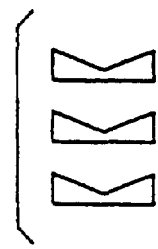
Figure 8D:
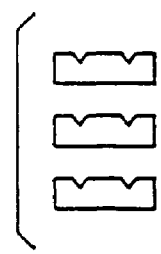
Figure 8E:
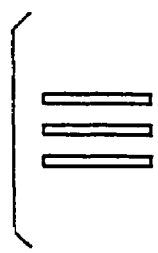
Figure 8F:
Figure 9A:
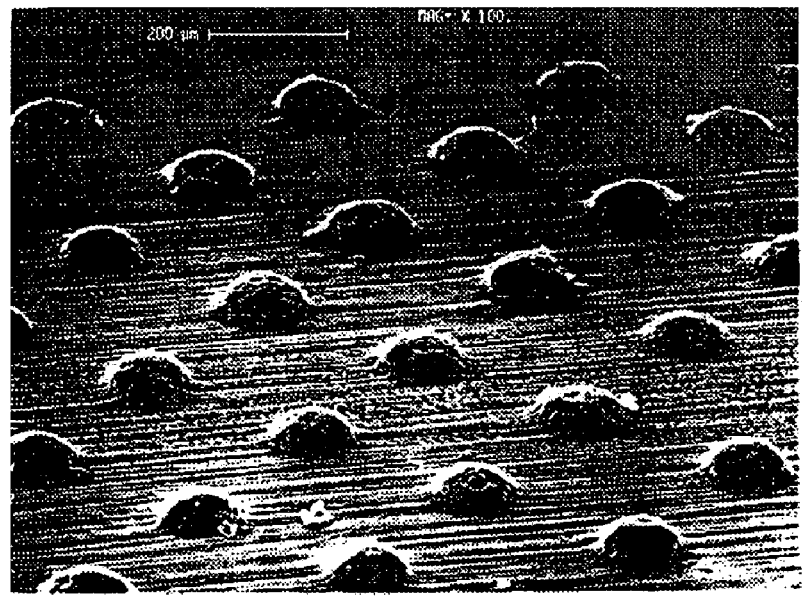
FIGS. 9A-D are views of preferred textured surfaces; as illustrated a textured surface can comprise texture structures which have curved or linear surfaces; the surfaces can be smooth or uneven. Exemplary texture structures are conical (FIGS. 9B-C), hexagons (FIG. 9D) or mounds (FIG. 9A). The structures depicted in FIG. 9 are broadly considered posts.
Figure 9B:
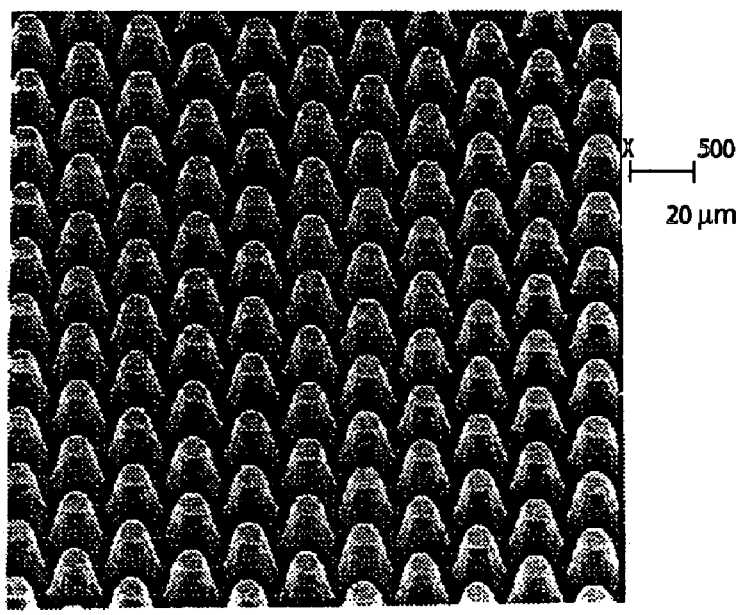
Figure 9C:
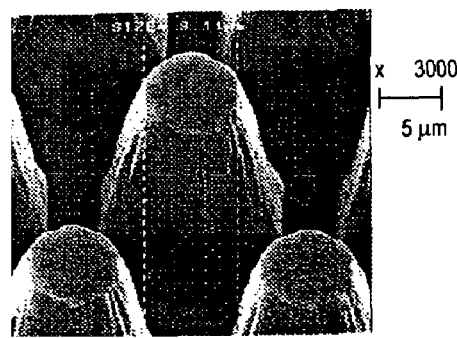
Figure 9D:
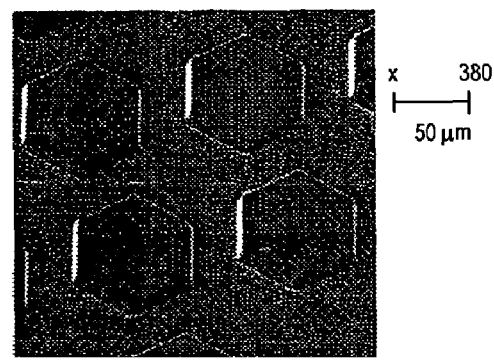
Figure 10:
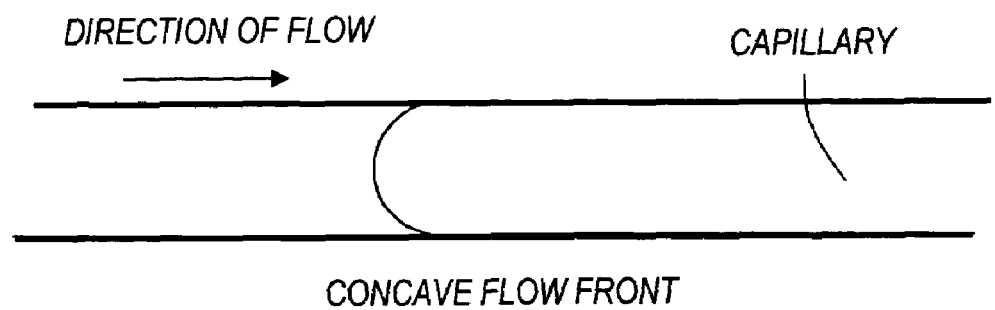
FIG. 10 depicts convex and concave flow fronts.
Figure 10:
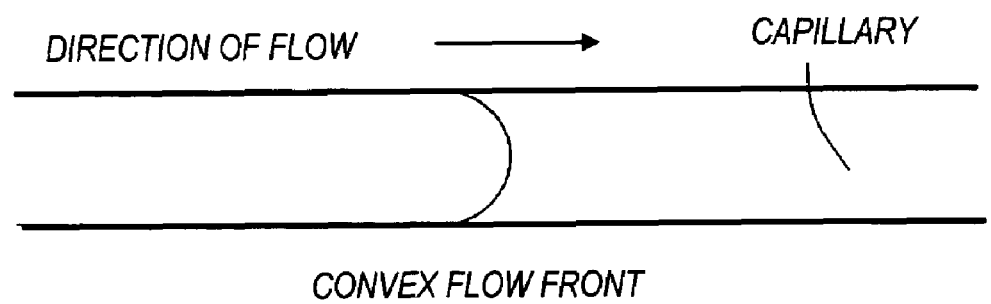

In an additional embodiment of the diagnostic element, now referring to FIG. 5, the diagnostic element 6 is a cylindrical surface which may be composed of grooves. When the diagnostic element is composed of grooves, the grooves generally run perpendicular to the flow of the reaction mixture. A capillary space is formed around the diagnostic element by a round tube which is generally clear; thus, the surface of the diagnostic element and the opposing surface of the tube are a capillary distance apart. The capillary formed allows the flow of the reaction mixture over the round diagnostic element 6. Generally, the reaction mixture would travel up against gravity or down with gravity through the cylindrical capillary space. The capture zones of the round diagnostic element 6 can be placed in discrete zones or over the entire length of the diagnostic element 6. The capture zones may also circle the diameter of the diagnostic element 6 or may be applied to only a radius of the diagnostic element 6. The reaction mixture may be delivered to the diagnostic element 6 through the tube 8. Furthermore, the cylindrical volume of the tube 8 may be used as a reaction chamber 4 and a disc shaped sample reaction barrier 3 with grooves on its perimeter may also be inserted to form the reaction chamber 4 and the sample addition reservoir 2. From this discussion, now referring to FIGS. 1 and 2, one skilled in the art can also appreciate that the flat diagnostic element 6 may also be curved such that the curvature is a radius of a circle.

One skilled in the art can appreciate that various means can be used for the detection of signal at the capture zone of the diagnostic element. In the case of the use of biosensors, such as, for example, a piezoelectric crystal, the piezoelectric crystal onto which would be immobilized a receptor, would be the capture zone and the response generated by binding target ligand would be generally reflected by an electrical signal. Other types of detection means include, but are not limited to visual and instrumental means, such as spectrophotometric and reflectance methods. The inventive features of the diagnostic element described herein allows for improved capture efficiencies on surfaces over which a reaction mixture flows and that various means for detection may be used by one skilled in the art. The surfaces of the capillaries in the device are generally hydrophilic to allow flow of the sample and reaction mixture through the device. In a preferred embodiment the surface opposing the diagnostic element 6 is hydrophobic such that the reaction mixture repels this surface. The repulsion of reaction mixture to the surface opposing the diagnostic element 6 forces the reaction mixture, and particularly the protein conjugates, to the surface where capture occurs, thus improving the capture efficiency of the components of the reaction mixture to the capture zone. The hydrophobic surfaces opposing the diagnostic element can have a tendency to become hydrophilic as the reaction mixture progresses through the diagnostic element because various components which may be present endogenously or exogenously in the sample or reaction mixture, such as, for example, proteins or polymers, bind to the hydrophobic surface. A preferred hydrophobic surface opposing the diagnostic element can be composed of TEFLON®. It is well known to those skilled in the art that TEFLON® surfaces bind proteins poorly. Thus, the TEFLON® surface opposing the diagnostic element would not become as hydrophilic as would surfaces composed of, for example, polystyrene, polyacrylate, polycarbonate and the like, when the reaction mixture flows through the diagnostic element.

In another preferred embodiment, the diagnostic element 6 is hydrophilic but the areas adjacent to the diagnostic element 6 are hydrophobic, such that the reagents of the assay are directed through only the hydrophilic regions of the diagnostic element. One skilled in the art will recognize that various techniques may be used to define a hydrophilic diagnostic element or zone, such as plasma treatment of hydrophobic surfaces using masks which shield the surfaces, except for the diagnostic element, from the treatment or by application of hydrophobic adhesives to hydrophilic surfaces to define a diagnostic element or by the use of viscous hydrophobic compounds, such as an oil or a grease. In another preferred embodiment, the capillary of the diagnostic element can be formed by ultrasonic welding. The boundaries of the diagnostic element are dictated by the energy directors which are used to form the sonicated weld.

The surfaces of the diagnostic element 6 or of the other components of the device may be smooth, grooved, or grooved and smooth. Various textured surfaces may also be employed, alone or in combination with smooth or grooved surfaces. For example, surfaces composed of posts, grooves, pyramids, and the like referred to as protrusions; or holes, slots, waffled patterns and the like, referred to as depressions may be utilized. Referring now to FIG. 9, the surface can comprise texture structures that comprise the form of diamonds, hexagons, octagons, rectangles, squares, circles, semicircles, triangles or ellipses. The textured surface can comprise texture structures in geometries ordered in rows, staggered or totally random; different geometries can be combined to yield the desired surface characteristics. Typically, the depressions or protrusions of the textured surface can range from about 1 nm to 0.5 mm and preferably from about 10 nm to 0.3 mm; the distance between the various depressions or protrusions can range from about 1 nm to 0.5 mm, and preferably from about 2 nm to 0.3 mm.

A surface of diagnostic element 6 may be smooth or comprised of texture structures such as posts or grooves. Texture on a device surface can facilitate drying of reagents on the surface during preparation of the device, and can facilitate movement of sample in the diagnostic element. Texture on a device surface facilitates uniform placement of dried reagents on the surface as follows: A liquid reagent-containing fluid is placed in contact with the textured surface, and small reagent fluid menisci form adjacent each texture structure. Absent the presence of texture, the fluid would tend to form larger menisci at corners of the entire surface or chamber, which when dried would cause a non-uniform layer of dried reagent. When texture structures are designed into the device, the presence of numerous small menisci leads to a more uniform layer of reagent that is dried throughout the surface or chamber.

In a preferred mode as shown in FIGS. 1 and 2, one surface of the diagnostic element 6 is grooved and the grooves are perpendicular to the flow of the reaction mixture and the opposing surface is smooth. In another embodiment, one surface of the diagnostic element 6 is grooved at the capture zone and the areas adjacent to the capture zone are smooth. The opposing surface of the diagnostic element 6 may be smooth or may be grooved, for example, the grooves of each surface intermesh. The positioning of the grooves of the diagnostic element perpendicular to the flow of the reaction mixture is beneficial in that the flow of the reaction mixture through the diagnostic element 6 occurs in an organized manner with a distinct, straight front dictated by the grooves in the capillary space.

In addition, when one surface is in close proximity, for example 1 µm to 100 µm, to the peaks of the grooves then the capture efficiency of the components from the reaction mixture can be enhanced. The enhancement of capture efficiency at the capture zones in grooved diagnostic elements as compared to smooth surface elements may be related to the movement of the reaction mixture in the capillary space; that is, in the case of the grooved surface the reaction mixture is forced to move over the peak of the groove and into the trough of the next groove. Thus, a finer grooved surface, that is, more grooves per cm, would provide a better capture efficiency than a coarser grooved surface. The reaction mixture is thus driven closer to the surface of the grooved diagnostic element than it would be if both surfaces were smooth.

Also, the close proximity of the surfaces decreases the volume of the bulk reaction mixture above the surface of the diagnostic element and therefore decreases the diffusion distance of the components which bind to the diagnostic element. The proximity of the surfaces of the diagnostic element should minimize the volume of reaction mixture in the diagnostic element at the capture zone without blocking the capillary flow through the element. In addition, in embodiments where a reagent is dried on a device surface and another reagent is dried on a separate surface of the device, these reagents can diffuse from their respective surfaces upon introduction of fluid to those surfaces. The surfaces having reagent immobilized thereon can be surfaces in a particular chamber of the device or can be surfaces in different regions of the device. The regions can be separate chambers or can be device surfaces that do not delimit a chamber.

The capture of, for example, the complex of target ligand: Ligand receptor conjugate at the capture zone can approach 100% efficiency if the proximity of the surfaces is optimized. The capture of nearly all of the ligand receptor conjugate which is bound by target ligand is most desired because a greater sensitivity of the assay as a function of sample volume can be achieved. Other advantages of improved capture efficiency are that less reagents are used because the sample volume is decreased, the assay device can be miniaturized because of the smaller sample volume and the reproducibility of the assay result will be improved because changes in the rate of flow of the reaction mixture through the capture zones will have less or no effect on the capture of the labeled conjugates.

The capillary space can be defined by a variety of ways, for example, machining the surfaces to the appropriate tolerances or using shims between the surfaces. In a preferred embodiment, ultrasonic welding of the surfaces defines the capillary. In this case, the capillary space is defined by the energy directors and the distance between the surfaces is a function of the size of the energy director, the welding energy, the time of energy application and the pressure applied during welding. The surfaces of the diagnostic element can be parallel or non-parallel. In the latter case, the flow rate of the reagents through the diagnostic element will not be uniform throughout the length. A preferred embodiment is to maintain the surfaces of the diagnostic element approximately parallel. The surfaces of the diagnostic element can be made from materials, such as plastics which are capable of being milled or injection molded, for example, polystyrene, polycarbonate, polyacrylate and the like or from surfaces of copper, silver and gold films upon which are adsorbed various long chain alkanethiols as described in *J. Am. Chem. Soc.* 1992, 114, 1990-1995 and the references therein. In this latter example, the thiol groups which are oriented outward can be used to covalently immobilize proteins, receptors or various molecules or biomolecules which have attached maleimide or alkyl halide groups and which are used to bind components from the reaction mixture for determining the presence or amount of the target ligand.

Figure 3A:
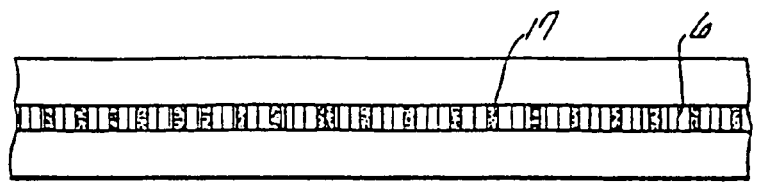
FIG. 3 is a partially schematic top view of the diagnostic element showing some potential placements of capture zones.
Figure 3B:
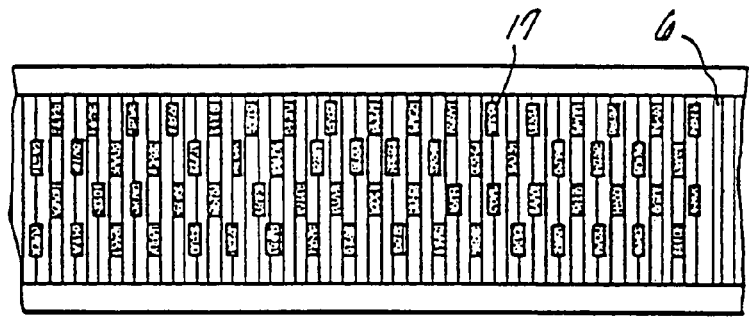

Referring to FIGS. 3A and 3B, the zones of immobilization of one or more receptors or the placement of biosensors at the capture zone 17 on the diagnostic element 6 can take many forms. For example, if the target ligand is very low in concentration in the sample then one would desire that all of the reaction mixture pass over the zone of immobilized receptor or biosensor to obtain the best signal from the given volume of reaction mixture. In this case, the placement of the reagents or biosensors on the diagnostic element 6 at the capture zones 17 could, for example, resemble that shown in FIG. 3A. If the target ligand in the sample is high in concentration and the sensitivity of the analytical method is not an issue then the placement of the receptors or biosensors at the capture zones 17 could, for example, resemble that in FIG. 3B. One skilled in the art can appreciate that the placement of receptors or biosensors on the diagnostic element is a function of the sensitivity requirements of the analytical method.

One or more diagnostic elements can be comprised in a device. The reaction mixture may be applied to a device with multiple diagnostic elements. In addition, the sample may be applied to the device and then separated into different reaction chambers, each with separate diagnostic elements. The capture zone can be various geometrical symbols or letters to denote a code when the sample is positive or negative for the target ligand. One skilled in the art will recognize the useful combinations of the elements of this invention.

The diagnostic element can also be configured to perform a semi-quantitative or quantitative assay, as for example, is described in *Clinical Chemistry* (1993) 39, 619-624, herein referred to by reference only. This format utilizes a competitive binding of antigen and antigen label along a solid phase membrane. The improvement is that the use of the diagnostic element described herein for the above cited method would require a smaller sample volume and improved binding efficiency to the solid phase surface.

Diagnostic Elements Other Than Capillaries

The inventive teachings described herein of the adsorption of proteins, particularly receptors to plastic surfaces, can be utilized for adsorption of receptors to many plastic surfaces which are not a part of a capillary. Nanoparticles and latex particles coated with receptors can also be applied to surfaces of many types of immunoassay devices, such as, to "dipsticks" or lidless devices. For example, dipsticks are generally a solid phase onto which are bound, as a result of the assay process, for example, the ligand receptor conjugate. Dipsticks generally incorporate membranes; however, a disadvantage in the use of membranes in dipsticks is the difficulty in washing the unbound ligand receptor from the membrane. Thus, an improvement in the use of dipsticks is to immobilize receptor coated latex or nanoparticles directly onto a plastic surface of the dipstick. The removal of unbound ligand conjugate from the plastic surface is thus more efficient than removal from a membrane.

Textured surfaces such as disclosed herein can be used in diagnostic elements other than capillaries. In such embodiments, a textured surface can serve to provide additional surface area which allows for a higher density of assay reagents to be immobilized thereon. Furthermore, a textured surface, or other surface modifications, can be provided to affect the flow characteristics of a fluid on or within the surface. For example, as disclosed herein a surface can be provided with hydrophobic regions to diminish the extent of fluid flow in the hydrophobic region, textures can be used that provide for a more uniform distribution of dried reagents on the surface, textures can be provided to modify the configuration of the meniscus at the fluid flow front, or textures can be used that provide the capillary driving force for movement of fluid within the surface.

Used Reagent Reservoir

Figure 4:
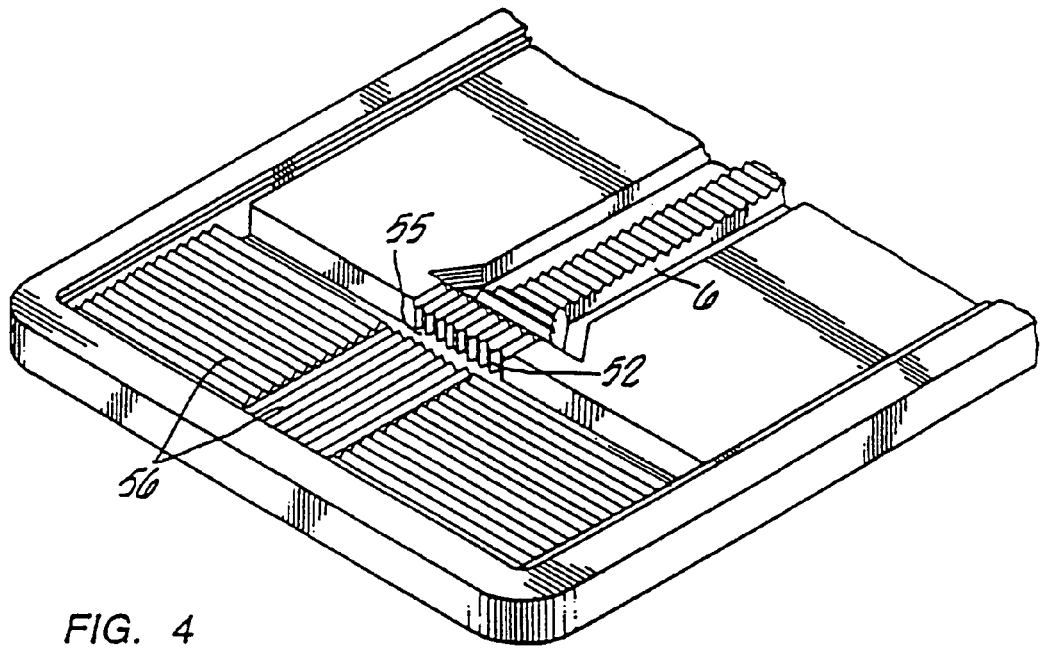
FIG. 4 is a partially schematic, perspective view of a used reagent reservoir.

Referring to FIGS. 1 and 2, the used reagent reservoir 7 receives the reaction mixture, other reagents and excess sample from the diagnostic element 6. The volume of the used reagent reservoir 7 is at least the volume of the sample and extra reagents which are added to or are in the device. The used reagent reservoir 7 can take many forms using an absorbent, such as a bibulous material of nitrocellulose, porous polyethylene or polypropylene and the like or the used reagent reservoir can be comprised of a series of capillary grooves. In the case of grooves in the used reagent reservoir 7, the capillary grooves can be designed to have different capillary pressures to pull the reagents through the device or to allow the reagents to be received without a capillary pull and prevent the reagents from flowing backwards through the device. The size and quantity of the grooved capillaries determine the volume and capillarity of the used reagent reservoir 7. In a preferred embodiment, as shown in FIG. 4, the fingers 52 at the end of the diagnostic element 6 are in fluid contact with a capillary space 55 and the capillary space 55 is in fluid contact with a grooved or textured capillary space 56. The depth of the grooves or textured surface can be, for example, about 0.1 mm to 0.6 mm, preferably about 0.3 mm to 0.5 mm and the density can range from about 5 to 75 grooves per cm and preferably about 10 to 50 grooves per cm.

Referring to FIG. 4, the reagents of the device move to the fingers 52 at the end of the diagnostic element 51 and into the capillary channel 55. The reagents either partially or completely fill the capillary space 55 and then come in contact with the grooved or textured surface 56. The width of the capillary space 55 is generally about 1 mm to 3 mm and the depth is generally about 0.1 mm to 2 mm. The length of the capillary space 55 should be sufficient to be in fluid contact with the grooved or textured surface 56. The grooved or textured surface 56 partially or completely pulls the reagents from the capillary channel 55 depending on the rate of delivery of the reagents into the capillary space 55 from the diagnostic element 51. When the flow of reagents is complete in the device, the grooved or textured surface 56 has greater capillarity than the capillary channel 55 and the reagents are removed from the capillary channel 55 by the grooved or textured surface 56. In addition, the reverse flow of the reagents from the grooved or textured surface is not preferred because the capillarity in the grooved or textured surface 56 holds the reagents and prevents their backward flow. One skilled in the art can recognize from these inventive features that the arrangement of grooves or a used reagent reservoir within the device can be adapted to a variety of desired objectives.

The Description of the One-Step Assay Device

The elements of the device which have been described individually can be assembled in various ways to achieve the desired function. The term "one-step" implies that one manual action is required to achieve the assay result, for example, adding sample to the device is one step. In the case of the device performing a one-step assay which involves both a timed incubation of reagents and a wash step, the wash solution is excess sample and the assay device is built with the elements in fluid communication using the sample addition reservoir, the sample-reaction barrier, the reaction chamber, the time gate, the diagnostic element and the used reagent reservoir as depicted in FIG. 1. The devices are generally about 3 cm to 10 cm in length, 1 cm to 4 cm in width and about 2 mm to 15 mm thick. Typically, a top member with smooth surfaces is placed onto a bottom member which has a surface onto which are built the elements stated above. The relationship of the elements are as depicted in FIG. 1. The reagents required for performing the assay are immobilized or placed in the respective elements. The surfaces are brought together, a capillary distance apart, and in doing so, the regions of the sample addition reservoir, the sample reaction barrier, the reaction chamber, the time gate, the diagnostic element, the gap and the used reagent reservoir are all formed and are capable of functioning together. Also, the surfaces are brought together such that the opposing surfaces touch to form and seal the sample addition reservoir, the reaction chamber, and the used reagent reservoir.

When performing a qualitative, non-competitive assay on one or more target ligands, the signal producing reagents, which could include, for example, a receptor specific for the target ligand adsorbed to a colloidal metal, such as a gold or selenium sol, are placed on the sample reaction barrier or in the reaction chamber in dried or lyophilized form. Another receptor for each target ligand is immobilized onto the surface of the diagnostic element at the capture zone. The time gate is positioned generally on the diagnostic element between the reaction chamber and the capture zones by the placement of, for example, a surfactant-free polystyrene suspension onto the device in an amount which dictates the desired incubation time. The incubation time is usually the amount of time for the reactions to come to substantial equilibrium binding. The assay is then performed by addition of sample to the sample addition reservoir of the device. The sample moves over the sample-reaction barrier, into the reaction chamber by the aid of the fingers and dissolves the reagents in the reaction chamber to form the reaction mixture. The reaction mixture incubates for the amount of time dictated by the time gate. The excess sample remaining in the sample addition reservoir and reaction mixture in the reaction chamber are in fluid communication but are not in substantial chemical communication because of the sample-reaction barrier. Thus, the reaction chamber defines the volume of the reaction mixture. The reaction mixture then moves past the time gate and onto the diagnostic element and over the capture zones. The complex of receptor conjugate and target ligand formed in the reaction mixture binds to the respective receptor at the capture zone as the reaction mixture flows over the capture zones. The reaction mixture may also flow over a positive control zone, which can be for example, an immobilized receptor to the signal development element. As the reaction mixture flows through the diagnostic element and into the used reagent reservoir by the aid of the fingers, the excess sample flows behind the reaction mixture and generally does not substantially mix with the reaction mixture. The excess sample moves onto the diagnostic element and removes the receptor conjugate which did not bind to the capture zone. When sufficient excess sample washes the diagnostic element, the signal at the capture zones can be interpreted visually or instrumentally. Referring to FIG. 1D, in a preferred mode of the above description, the reaction mixture moves onto the diagnostic element 6, over the capture zone or zones and then the reaction mixture proceeds into a capillary gap 18. The capillary gap 18 generally has less capillarity than that of the diagnostic element 6. The capillary space 19 of the diagnostic element 6 is generally smaller than the capillary space of the gap 18. The volume of the capillary gap 18 generally approximates the volume of the reaction mixture such that the capillary gap 18 fills slowly with the reaction mixture and once filled, the capillarity of the remaining portion of the diagnostic element 6 or used reagent reservoir is greater than the capillarity of the gap 18 resulting in an increased rate of flow to wash the diagnostic element 6. As one skilled in the art can appreciate, the gap 18 can be formed in the top member 8 or in the bottom member 9 or a combination of both members 8 and 9.

In the case of the device performing a one-step assay which does not involve a timed incubation step but does involve a wash step in which the wash solution is excess sample, the assay device is built with the elements in fluid communication using the sample addition reservoir, the sample-reaction barrier, the reaction chamber, the diagnostic element and the used reagent reservoir. The assay reagents are used as described above for the non-competitive qualitative assay. The assay device without the time gate allows the reaction mixture to flow onto the diagnostic element without an extended incubation time. The capillary flow of the reaction mixture and the excess sample are as described above.

The optional reagent chamber is incorporated into the device in the case of the device performing a one-step assay with the introduction of an additional assay reagent into or after the reaction mixture or the introduction of a wash solution which flows behind the reaction mixture through the device. The optional reagent chamber may be in fluid contact with any element of the device and is generally in fluid contact with the reaction chamber. When in fluid contact with, for example, the reaction chamber, the optional reagent chamber and the reaction chamber may be separated by a time gate. Various reagents may be dried or lyophilized in the optional reagent chamber, such as detergents for a washing step or reagents which are sequentially provided to the diagnostic element after the reaction mixture.

In the case of performing one-step, non-competitive, quantitative assays the reagents as described above for the non-competitive, qualitative assay may apply. The device is comprised of the elements, sample addition reservoir, sample-addition barrier, reaction chamber, time gate, diagnostic element and used reagent reservoir. In this case, the capture zone of the diagnostic element is generally the entire diagnostic element. That is, the capture zone is a length of the diagnostic element onto which the receptor conjugate binds. The receptor conjugate binds along the length of the capture zone in proportion to the amount of target ligand in the sample. Alternatively, one or more capture zones 17 can be placed on the diagnostic lane (FIGS. 3A-B), and signals from the capture zone(s) can be read by an instrument such as a CCD camera, a fluorometer or a spectrophotometer.

The device of the present invention is preferred for this quantitative assay because of the high efficiency of capture of the reagents, for example, the binding of a complex of target ligand and receptor conjugate to an immobilized receptor to the target ligand on the capture zone, and because the movement of the reaction mixture over the diagnostic element proceeds with a sharp front. The receptors on the capture zone sequentially become saturated with the complex of target ligand and receptor conjugate as the reaction mixture moves over the length of the capture zone. The length of the diagnostic element containing bound conjugate then determines the concentration of the target ligand. Those skilled in the art will recognize the format of this type of immunoassay as a quantitative immunochromatographic assay as discussed in U.S. Pat. Nos. 4,883,688 and 4,945,205, hereby incorporated by reference.

In the case of the device performing a one-step, quantitative or qualitative competitive assay which involves both a timed incubation of reagents and a wash step and the wash solution is excess sample, the assay device is built with the elements in fluid communication using the sample addition reservoir, the sample-reaction barrier, the reaction chamber, the time gate, the diagnostic element and the used reagent reservoir. When performing a qualitative competitive assay on one or more target ligands, the conjugate is composed of, for example, a ligand analogue coupled to signal development element, such as a gold or selenium sol. The conjugate and receptor for each target ligand are placed in the reaction chamber in dried or lyophilized form, for example, in amounts which are taught by U.S. Pat. Nos. 5,028,535 and 5,089,391, hereby incorporated by reference. Another receptor for each target ligand is immobilized onto the surface of the diagnostic element at the capture zone. The time gate is positioned generally on the diagnostic element between the reaction chamber and the capture zones as described previously. The incubation time is usually the amount of time for the reactions to come to substantial equilibrium binding.

The assay is then performed by addition of sample to the device. The sample moves over the sample-reaction barrier and into the reaction chamber, dissolves the reagents to form the reaction mixture and incubates for the time dictated by the time gate. The excess sample and reaction mixture are in fluid communication but not in substantial chemical communication because of the sample-reaction barrier. The reaction mixture then moves onto the diagnostic element and over the capture zones. The ligand analogue conjugate binds to the respective receptor or receptors at the capture zone or zones. As the reaction mixture flows over the diagnostic element and into the used reagent reservoir, the excess sample flows behind the reaction mixture and generally does not substantially mix with the reaction mixture. The excess sample moves onto the diagnostic element and removes conjugates which do not bind to the capture zone or zones. When sufficient excess sample washes the diagnostic element the results at the capture zones can be interpreted visually or instrumentally.

In a preferred mode of the present invention, the reaction mixture moves onto the diagnostic element, over the capture zone or zones and then the reaction mixture proceeds into a capillary gap. The capillary gap has less capillarity than that of the diagnostic element. The volume of the capillary gap generally approximates the volume of the reaction mixture such that the capillary gap fills slowly with the reaction mixture and once filled, the capillarity of the remaining portion of the diagnostic element or used reagent reservoir is greater resulting in an increased rate of flow of excess sample to wash the diagnostic element.

In another aspect of the one-step, competitive assay, the reaction mixture is composed of ligand analogue-ligand complement conjugate to each target ligand and receptors adsorbed to latex particles with diameters of, for example, 0.1 µm to 5 µm to each target ligand, in appropriate amounts, for example, as taught by U.S. Pat. Nos. 5,028,535 and 5,089,391. The ligand complement on the conjugate can be any chemical or biochemical which does not bind to the receptors for the target ligands. The assay is begun by addition of sample to the device. Sample fills the reaction chamber and is incubated for a time which allows the reagents to come to substantial equilibrium binding. The reaction mixture flows over the time gate and onto or into a filter element to prevent ligand analogue-ligand complement conjugates which have bound to their respective receptor latexes from passing onto the diagnostic element. Typical filter elements can be composed of nitrocellulose, cellulose, nylon, and porous polypropylene and polyethylene and the like. Thus, only the ligand analogue-ligand complements conjugate which were not bound by the receptor latex will pass onto the diagnostic element. The receptor to the ligand complement of the conjugate is immobilized on the diagnostic element at the capture zone and binds the conjugate. A wash step may not be required because the filter removes the conjugate bound to latex; however, the excess sample or a wash solution from the optional reagent chamber may be used to wash the diagnostic element.

In the case of a one-step quantitative, competitive assay, the receptor to the ligand analogue conjugate or the ligand complement of the conjugate is immobilized onto the diagnostic element as described previously for the one-step quantitative, non-competitive assay. Thus, the concentration of the target ligand in the sample is visualized by the distance of migration on the diagnostic element of the conjugate. In another mode, a quantitative assay could be performed by the binding of the labeled conjugate, for example, the ligand analogue-ligand complement conjugate, to sequential, discrete capture zones of receptor on the diagnostic element. The quantitative result is achieved by the depletion of the conjugate as the reaction mixture flows through the capture zones of the diagnostic element. Signal related to analyte concentration is measured, e.g., by a CCD camera, a fluorometer or a spectrophotometer.

The Device as a Diagnostic Element

The diagnostic element of the device can be utilized with a sample addition means to perform a separation step of bound and unbound conjugates. An example of this type of device which has a sample addition means, a diagnostic element and a used reagent reservoir is depicted in FIG. 2. For example, in the case of a non-competitive assay, at least one receptor conjugate is incubated with sample which is suspected of containing at least one target ligand in a suitable vessel and this reaction mixture is applied to the sample addition zone of the device. The reaction mixture then flows onto the diagnostic element and over the capture zone of, for example, immobilized receptor to the target ligand. When target ligand is present in the sample, the target ligand-receptor conjugate complex binds to the receptor on the capture zone. If the signal development element is an enzyme, then either a substrate for the enzyme which produces a visual color or a wash solution followed by a substrate is next added to the device. Excess reagents flow to the used reagent reservoir. The presence or amount of each target ligand in the sample is then determined either visually or instrumentally.

In the case of a competitive immunoassay, for example as taught by U.S. Pat. Nos. 5,028,535 and 5,089,391, herein incorporated by reference, the diagnostic element may be used to separate bound and unbound ligand analogue conjugates such that the unbound ligand analogue conjugates bind to the receptors of the diagnostic element in proportion to the presence or amount of target ligand in the sample.

One skilled in the art can appreciate that all formats of immunoassays or nucleic acid assays which require a separation step of free and bound conjugates or the separation of free of bound reagents which subsequently leads to the ability to detect a signal can utilize the inventive features of the diagnostic element. One skilled in the art can also recognize that the inventive elements of this invention, namely, the fingers, the sample reaction barrier, the reaction chamber, the time gate, the diagnostic element, the fluid control means and the used reagent reservoir can be used separately or in various combinations and in conjunction with other devices not described here. Furthermore, textured surfaces, such as described herein, can be utilized in one or more regions of the device to facilitate placement of a uniform layer of dried reagent in the area, or to modify fluid flow characteristics through the region. In addition, hydrophobic zones can be placed in a region of the device to modify fluid flow characteristics in the region. As appreciated by one of ordinary skill in the art, features disclosed herein can be utilized in various combinations in the preparation and use of assay devices.

For example, the sample reaction barrier with fingers and the reaction chamber can be used in conjunction with devices incorporating porous members, such as membranes to deliver precise volumes of reagents to the porous member. The time gate can also be incorporated into the aforementioned devices or the time gate may be used alone in conjunction with devices incorporating porous members. The fluid control means can also be used in devices incorporating porous members to control the rate of flow of reagents through the porous member. In the context of performance of assays in accordance with the invention, channels can exist such as the distance between opposing walls of a particular region, e.g., between the lid and the base; or the distance between adjacent texture structures. Accordingly, when a ligand receptor is immobilized on a device surface, a ligand of interest in a sample can diffuse across the width of a channel to bind with its receptor.

EXAMPLES

Example 1

Preparation of Anti-βhCG Antibody-Colloidal Gold Conjugate

Colloidal gold with an average diameter of 45 nm was prepared according to the method of Frens, *Nature, Physical Sciences*, 241, 20 (1973). The colloidal gold conjugate was prepared by first adding 5.6 ml of 0.1 M potassium phosphate, pH 7.58, dropwise with rapid stirring to 50 ml of colloidal gold. Anti β-subunit monoclonal antibody to hCG (Applied Biotech, San Diego, Calif.; 1 ml of 4.79 mg/ml in phosphate buffered saline, 0.02% sodium azide, pH 7) was added in a bolus to the colloidal gold with rapid stirring. After complete mixing the stirring was stopped and the solution was incubated at room temperature for 1 h. Polyethylene glycol (average molecular weight=20,000) was added (0.58 ml) as a 1% solution to the colloidal gold solution and the solution was mixed. The colloidal gold solution was subjected to centrifugation at 27,000 g and 5 C for 20 min. The supernatant was removed and each pellet was washed twice by resuspension and centrifugation with 35 ml of 10 mM potassium phosphate, 2 mM potassium borate, 0.01% polyethylene glycol (average molecular weight=20,000), pH 7. After the final centrifugation, the pellet was resuspended in 0.5 ml of the wash buffer. The gold conjugate was diluted for the assay of hCG into a buffered solution containing 10 mg/ml bovine serum albumin at pH 8.

Example 2

Preparation of Anti-hCG Antibody Latex

Surfactant-free polystyrene particles (Interfacial Dynamics Corp., Portland, Oreg.; 0.106 ml of 9.4% solids, 0.4 μm) was added while vortexing to anti α-subunit hCG monoclonal antibody (Applied Biotech, San Diego, Calif.; 0.89 ml of 6.3 mg/ml in 0.1 M 2-(N-morpholino) ethane sulfonic acid, (MES), pH 5.5) and the suspension was incubated at room temperature for 15 min. The suspension was subjected to centrifugation to pellet the latex particles. The pellet was washed three times by centrifugation and resuspension of the pellet with 10 mM MES, 0.1 mg/ml trehalose, pH 5.5. The final pellet was resuspended in the wash buffer at a solids concentration of 1%.

Example 3

Preparation of Goat Anti-Mouse Latex

Surfactant-free polystyrene particles (Interfacial Dynamics Corp., Portland, Oreg.; 0.11 ml of 9.4% solids, 0.6 μm) were added while vortexing to goat IgG antibody against mouse IgG (Jackson ImmunoResearch Laboratories, Inc.; 0.89 ml of 0.34 mg/ml in 0.1 M MES, pH 5) and the suspension was incubated at 45° C. for 2 h. The suspension was subjected to centrifugation to pellet the latex particles. The pellet was washed three times by centrifugation and resuspension of the pellet with 10 mM MES, 0.2 mg/ml trehalose, pH 5.5. The final pellet was resuspended in the wash buffer at a solids concentration of 1%.

Example 4

Preparation of the One-Step, Device for a Qualitative or Quantitative hCG Assay

A one-step device made of plastic was built having an 80 to 100 μl sample addition reservoir, a 20 μl reaction chamber and a 40 μl used reagent reservoir. This device is designed for applying samples of about 20 μl to 100 μl, but the reaction chamber is fixed at 20 μl. In cases where a larger reaction mixture volume is required for the desired assay, then the reaction chamber would be increased to that volume and the sample addition reservoir would be about 2 to 4 times the volume of the reaction chamber volume.

The devices were plasma treated to graft functional groups which create a hydrophilic surface. Those skilled in the art will recognize that the plasma treatment of plastic is performed in a controlled atmosphere of a specific gas in a high frequency field. The gas ionizes, generating free radicals which react with the surface.

The sample addition reservoir was shaped as a trapezoid with dimensions of 14 mm and 7 mm for the parallel sides and 7 mm for the other sides with a depth of 0.49 mm. The sample addition reservoir was adjacent to the sample reaction barrier.

The sample-reaction barrier was 1.5 mm long and 7 mm wide including grooves running parallel to the flow of the sample at a density of 50 grooves per cm and a depth of 0.1 mm. In the case of sample volumes larger than 20 to 80 μl, the width of the reaction barrier and thereby the reaction chamber could be increased to accommodate the desired flow rate but the groove size or density could remain as indicated.

The fingers in the walls of the reaction chamber and the used reagent reservoir were 1 mm wide and 0.4 mm deep with 7 fingers in each wall of the reaction chamber and the used reagent reservoir. The reaction chamber volume was 20 μl. The reaction chamber was shaped as a trapezoid with dimensions of 7 mm and 3.5 mm for the parallel sides and 7.1 mm for the other sides with depths of 0.56 mm for 20 μl reaction chambers.

The diagnostic element was about 2.5 cm long, 2 mm wide and 1 mm from the base of the device including grooves running perpendicular to the flow of reaction mixture at a density of 100 grooves per cm and a depth of 0.05 mm. In the case of a time gate on the diagnostic element, the time gate was positioned on the diagnostic element immediately adjacent to the reaction chamber. The width of the diagnostic element could be increased to increase the flow of the reaction mixture to the desired rate past the capture zones.

The anti-αhCG antibody latex (1 μL) and the goat anti-mouse latex (1 μl) were applied to the diagnostic element of the devices approximately 1.5 cm apart. The anti-βhCG antibody colloidal gold conjugate (10 μl) was pipetted into the trough of the reaction chamber.

The devices were placed under vacuum for about 15 min. to dry the reagents. The used reagent reservoir had the shape of a trapezoid with dimensions of 7 mm and 15 mm for the parallel sides and 8 mm for the other sides with a depth of 0.5 mm.

Referring to FIG. 4, in a preferred embodiment of the used reagent reservoir, the reaction mixture moved to a capillary space 55 (1.25 mm long, 27.5 mm wide and 0.48 mm deep) from the diagnostic element 6, aided by fingers 52 (1 mm wide and 0.4 mm deep with 7 fingers), and then into a grooved capillary structure (13.6 mm long, 25.4 mm wide, 0.61 mm deep with a density of 16 grooves per cm). The outer walls and the top surface of the walls of the sample addition reservoir and the reaction chamber had applied a thin coating of silicon grease to prevent the leakage of the reagents from the reservoir and chamber of the assembled device. The capillary spaces in the devices were then formed by placing a clear plastic polycarbonate sheet on top of the device. The plastic sheet was held to the opposing surface with binder clips. The clear plastic sheet had a sample port above the sample addition reservoir for the introduction of sample.

Example 5

Hydrophobic Borders to Fluid-Containing Areas

Fluid flow on a surface or in a capillary is affected by the surface tension of the fluid. For example, in a capillary channel that is formed by essentially planar walls that intersect along corners, fluid flow preferentially precedes along the corners. The predisposition for fluid flow to proceed at corners occurs because the corners of a capillary create the lowest surface tension for the fluid.

However, when a uniform flow front is required within a capillary, the reduced surface tension at corners of the capillary can cause a non-uniform flow front. Non-uniform flow fronts can result in the creation of air pockets within the capillary. If air pockets occur, wetting of the capillary surfaces within the air pocket is impaired or prevented. Consequently, when surfaces of capillaries are used, for reactions such as binding of antibodies or antigens, for chemical reactions, or for nucleic acid hybridization reactions, the creation of air pockets decreases the efficiency of the reaction. Furthermore, the creation of air pockets within analogous capillaries of individual devices of the same design is not predictable, consequently the consistency of binding or chemical reactions between the individual devices will be poor. Thus, air pockets within capillaries can alter fluid flow or even prevent it in the capillary.

Embodiments of this invention which comprise hydrophobic areas on a lumenal surface of a capillary space act to control fluid flow within capillaries, and more specifically to minimize fluid flow at the corners of capillaries so that the fluid flow front is convex rather than concave.

The inventive teachings herein show that hydrophobic borders lining capillary channels, preferably along edges or at corners, slows fluid flow at these locations, thereby creating convex flow fronts instead of the native concave flow front. Concave flow fronts are disadvantageous in capillary channels because air can be trapped as the concave flow front proceeds through the capillary, since a concave flow front increases the propensity of the advancing fluid to form air pockets in the capillary. Hydrophobic borders facilitate the escape of air from the advancing fluid flow front because the likelihood is substantially reduced that fluid can be held within the capillary in the hydrophobic zones.

In a preferred embodiment, hydrophobic zones are applied to a surface. Specifically, a hydrophobic zone can be located on at least one surface of a capillary, each hydrophobic zone bordering the edge or corner of the capillary, being located adjacent a hydrophilic surface in which fluid is intended to flow. On at least one surface of the capillary, the hydrophobic zones or borders occupy between 1% to 90% of the surface, each zone being adjacent to a hydrophilic surface and the edge or corner of the capillary.

Hydrophobic zones delimit the edges of a surface or occupy the edges of materials placed in capillary spaces. In another preferred embodiment, hydrophobic zones delimit the edges of materials placed in capillary spaces, for example, materials such as filters, membranes and polymeric meshes. The hydrophobic zone can cover from 1% to 90% of the surface of the material to be placed in the capillary space. For additional disclosure concerning the use of materials within capillary spaces, see e.g., copending U.S. application Ser. No. 08/704,804 filed 26 Aug. 1996, which is incorporated by reference herein. Accordingly, fluid flow in the capillary is delayed at the edges of the material in contact with the corners of the capillary relative to the fluid flow within the hydrophilic zones of the capillary. The hydrophobic zones of the material in the capillary occupy between 1% and 90% of the surface of the material, each zone being adjacent to the hydrophilic surface and the edge of the capillary.

In addition, embodiments of the invention allow for the application of fluids to discrete zones on surfaces or within surfaces or membranes. Thus, in another preferred embodiment hydrophobic zones of surfaces prevent the movement of reagents on or within a surface or within a membrane. In this embodiment, these zones act as corrals to hold fluid within an area of the surface. These embodiments overcome a difficulty of applying reagents to discrete zones on or within surfaces or in membranes, such that a volume of applied reagent will move on a surface or within a membrane because of the hydrostatic pressure of the reagent. This problem is especially prevalent in the case of surfaces which comprise a texture to facilitate movement of fluids by capillary action along the surface such as during the performance of an assay on a fluid sample. However, when manufacturing such assay devices, it can be desirable to place reagents on such surfaces, application of discrete zones of reagents is especially difficult because the surface is designed to facilitate fluid movement by capillary action, and the effects of hydrostatic forces exacerbate the difficulties produced by capillary action. These factors create an unpredictable area of reagent, which may not be discrete. Consequently, if the volume of the applied reagent relative to the surface is too great, adjacent reagent areas may run together to create one undesired, commingled zone. This situation is particularly problematic when the surface comprises grooves or texture that cause fluids to flow by capillarity on or within the surface. Generally, such surfaces are substantially fluid impermeable. Accordingly, the creation of hydrophobic borders on or within a surface or in a membrane to encompass or retain the applied reagent allows the application of reagents in discrete areas.

In another preferred embodiment, hydrophobic zones are applied to surfaces to control the overall movement of the fluid on or within a surface or in a capillary. For example, hydrophobic zones can be utilized to direct or prevent fluid flow to various areas of a device.

In an alternative preferred embodiment, hydrophobic borders are placed at the edge(s) of a surface such as adjacent to corners of a chamber, to facilitate uniform drying of liquids on the surface. This embodiment is useful in the drying of liquid on a surface, wherein, in the absence of hydrophobic borders, liquid which is added to the surface or chamber accumulates at the edge or corners of the surface or chamber as evaporation occurs. This latter situation occurs because the corners of a chamber create a meniscus and it is energetically favorable for a fluid to move to a corner meniscus as it evaporates. Therefore, the outcome of evaporation is a disproportionately larger amount of dried reagent in the corners of the chamber than in the surface of the chamber. The novel use of hydrophobic borders adjacent to corners of chambers prevents the fluid meniscus from forming at the corner, since the fluid will not accumulate at the hydrophobic border. Thus, by use of this embodiment, the resultant dried liquid is more uniformly dispersed on the floor of the chamber.

Hydrophobic zones can also be created for surfaces which had previously been made hydrophilic. Several techniques are known to those skilled in the art for use to make a surface hydrophilic, for example, corona discharge, treating with a gas plasma, treating with detergents or proteins and the like. For surfaces made hydrophilic by the aforementioned techniques, hydrophobic zones can be created by application of organic solvents that destroy the plasma treatment or denature the proteins, to recreate a native hydrophobic plastic surface or to create a hydrophobic surface by the denatured proteins, or by local heating of the surface using focused laser beams to destroy the hydrophilic nature of the surface. Alternatively, one can mask hydrophobic areas before creating a hydrophilic area by any of the foregoing methods. The areas can be masked by objects such as a template or can be masked by materials that are applied to the surface and then are subsequently removed.

Hydrophobic compounds, such as aliphatic and/or aromatic compounds and various inks and polymers and the like can be used for the creation of hydrophobic zones in accordance with the invention. The compounds are generally dissolved in organic solvents or mixtures of aqueous and organic solvents. One skilled in the art will recognize that a variety of techniques known in the art (such as ink jet printing, spraying, silk screening, drawing, embossing and the like) are techniques that permit the application of hydrophobic zones on or within surfaces.

Example 6

Textured Surfaces to Facilitate Uniform Drying of Reagents

In an additional embodiment, texture structures such as posts are positioned, generally in an ordered array on a surface. When fluid is placed in contact with the structures, small menisci are formed at each structure. When the reagent fluid dries, these menisci thereby provide a very uniform distribution of dried reagent on the surface. Generally, the structures are posts which are substantially perpendicular to a surface such as a floor of a chamber. A rectilinear angle is defined between a surface and a wall of a post located thereon. The density and size and shape of posts on the surface can vary, depending on the degree of uniformity desired for the dried reagents. Post height can also vary, and generally the height of the posts should be about 1% to more than 100% of the height of the fluid in the chamber; that is, the posts can protrude from the fluid or the fluid can cover the posts after applying the fluid to the surface. In all cases, the posts will act as zones to form menisci as liquid evaporates from the surface or chamber.

Example 7

Qualitative or Quantitative One-Step Assay for hCG

The devices described in Example 4 were used for the qualitative or quantitative one-step assay for hCG. The assay times for the devices without the time gates were about 5 to 10 min. A urine solution (60 µl) containing 0, 50, 200 and 500 mIU hCG/ml was added to the sample reservoir of the devices. The sample moved into the reaction chamber, dissolved the colloidal gold conjugate and the reaction mixture moved onto the diagnostic element over the anti-hCG latex and goat anti-mouse IgG latex capture zones. The reaction mixture moved into the used reagent reservoir and the excess sample washed the diagnostic element. The color density of the capture zones for hCG was measured instrumentally using a MINOLTA CHROMA METER CR 241 at 540 nm. A red color was visible for samples containing hCG and not visible for the sample without hCG at the capture zones for hCG. The _E* values for the 0, 50, 200 and 500 mIU/ml were 0, 7.78, 12.95 and 20.96, respectively, and for the positive control (goat anti-mouse IgG) zones a distinctive red bar was observed with a _E* of about 35.

Example 8

Qualitative or Quantitative One-Step Assay for hCG Using a Time Gate

Devices as described in Example 4 were prepared with the addition of the time gate. The time gate was formed on the diagnostic element which is in contact with the reaction mixture in the reaction chamber.

The time gate was prepared by adding 1 μl of 2% solids of surfactant-free, sulfated latex, 1.0 μm, (Interfacial Dynamics Corp., Portland, Oreg.). The other reagent latexes and gold conjugate were also added to the devices and dried as described in Example 7. Clear plastic sheets were placed on the devices and various aliquots of sample (about 60 μl) containing 0, 50, 200 and 500 mIU hCG/ml, respectively, was added to the devices.

The sample moved into the reaction chamber, dissolved the colloidal gold conjugate and the reaction mixture remained in the reaction chamber for about 8 to 10 min, whereas in devices without time gates the reaction mixture remained in the reaction chamber for 5 sec to 15 sec. The proteinaceous components of the reaction mixture, which may be present in the sample and which was added as a component of the reaction mixture, namely, bovine serum albumin, bound to the latex particles of the time gate and changed the hydrophobic surface of the time gate into a hydrophilic surface. Other proteins, such as gelatin, serum albumins, immunoglobulins, enzymes and the like and polypeptides and hydrophilic polymers will also function to bind to the hydrophobic zone.

The gradual transformation of the hydrophobic surface to a hydrophilic surface, which resulted through binding of the proteinaceous components of the reaction mixture to the latex particles allowed the reaction mixture to flow over the area of the time gate.

In control experiments in which protein, namely bovine serum albumin, was not added to the reaction mixture, flow of the reaction mixture over the time gate and onto the diagnostic element did not occur during the time (5 h) of the experiment. This control experiment showed that the urine sample alone did not contain sufficient protein or components which bind to the applied latex of the time gate to allow a change in the hydrophobic character of the time gate. In the event that the components in the sample should only be used to cause the transformation of the hydrophobic time gate to a hydrophilic one for the reaction mixture to flow, then one would be required to lower the mass and total surface area of the latex applied to the time gate to an extent which would allow flow of the reaction mixture over the time gate in an appropriate amount of time.

The reaction mixture then moved onto the diagnostic element over the anti-hCG latex and goat anti-mouse IgG latex capture zones. The reaction mixture moved into the used reagent reservoir and the excess sample washed the diagnostic element. The color density of the capture zones for hCG was measured instrumentally using a MINOLTA CHROMA METER CR 241. A red color was visible for samples containing hCG and not visible for the sample without hCG at the capture zones for hCG. The _E* values for the 0, 50, 200 and 500 mIU/ml were 0, 6.51, 13.14 and 18.19, respectively. A red color bar was visible at the goat anti-mouse IgG capture zones of each device.

Example 9

Qualitative or Quantitative One-Step Assay for hCG Using a Flow Control Means

Devices as described in Example 4 were prepared with the addition of the optional flow control means.

The optional flow control means or "gap" was placed behind the capture zone for hCG gold conjugate on the diagnostic element. The gap between the two surfaces was 0.38 mm, the length of the gap was 13.2 mm and the width of the gap on the top member was 9 mm; however, the effective width of the gap was the width of the diagnostic element (2 mm). This gap volume above the diagnostic element was about 10 μl which was, in this case, half the volume of the reaction chamber.

The anti-hCG and the goat anti-mouse latexes and gold conjugate were added to the device and dried as described in Example 7. Clear plastic sheets of polycarbonate having a gap in one surface were placed on the devices with the gap facing the diagnostic element. Sample (about 60 μl) containing 0 and 200 mIU hCG/ml was added to the devices. The sample moved into the reaction chamber, dissolved the colloidal gold conjugate and the reaction mixture then moved onto the diagnostic element over the anti-hCG latex. The reaction mixture then entered the gap which was immediately behind the capture zone of anti-hCG latex. The flow rate over the capture zone slowed while the reaction mixture moved over the capture zone and filled the gap. The time for the 10 μl reaction mixture to fill the gap was about 12 min to 16 min, whereas with devices without the optional flow control means, the times were about 1 min to 3 min. for the reaction mixture to pass over the capture zone. When the reaction mixture filled the gap, the reaction mixture then moved into the narrow capillary of the diagnostic element and over the goat anti-mouse capture zone. The reaction mixture moved into the used reagent reservoir and the excess sample washed the diagnostic element.

The color density of the capture zones for hCG was measured instrumentally using a MINOLTA CHROMA METER CR 241. A red color was visible for samples containing hCG and not visible for the sample without hCG at the capture zones for hCG. The _E* values for the 0 and 200 mIU/ml were 0 and 16.12. The E* value of the hCG capture zone for the device without the flow control means for the 200 mIU/ml sample was 16.32. A red color bar was visible at the goat anti-mouse IgG capture zones of each device.

Example 10

Preparation of the Diagnostic Element for Multi-Step Assays

A device was built comprising a sample addition reservoir and a diagnostic element. The devices were plasma treated to graft functional groups which create a hydrophilic surface. The sample addition reservoir had dimensions of 12 mm long, 6 mm wide and 0.05 mm deep. The diagnostic element was about 5.5 cm long, 1.3 mm wide and 1 mm from the base of the device and included grooves running perpendicular to the flow of reaction mixture at a density of 100 grooves per cm and a depth of 0.05 mm. In the case of qualitative assays, the antibody latex (1 μl) was applied to the diagnostic element, covering the entire width and 1 cm length of the diagnostic element. In the case of an immunochromatographic assay, the antibody latex (6 μl) was applied to the entire width and length of the diagnostic element. The devices were placed under vacuum for about 1 h to dry the reagents. The capillary spaces in the device were then formed by placing a clear plastic polystyrene sheet on top of the device. The plastic sheet was held to the opposing surface with binder clips.

Example 11

Assay for hCG Using the Diagnostic Element

The diagnostic element described in Example 10 was used for the assay of hCG. Urine samples (20 μl) containing 0, 50, 200 and 500 mIU/ml hCG were added to tubes containing anti-βhCG antibody colloidal gold conjugate (2 μl). The tubes were vortexed and the reaction mixtures were incubated for 5 min at room temperature. The reaction mixtures (20 μl) were applied in 10 μl aliquots to the sample addition reservoir of the device. The reaction mixture flowed onto the diagnostic element from the sample reservoir and over the capture zone. An absorbent at the end of the capture zone removed the used reagent from the diagnostic element. The color density of the capture zones for hCG was measured instrumentally using a MINOLTA CHROMA METER CR 241. A red color was visible for samples containing hCG and not visible for the sample without hCG at the capture zones for hCG. The _E* values for the 0, 50, 250 and 500 mIU/ml were 0.00, 1.24, 3.16 and 5.56, respectively.

Example 12

Synthesis of meta-Nitrophencyclidine

To an ice cooled solution of phencyclidine hydrochloride (5 g, $1.8 \times 10^{-2}$ mol) in concentrated sulfuric acid (9 ml) was added dropwise, and with stirring, fuming nitric acid (2 ml). The reaction mixture was stirred in an ice-water bath for 1 hour and then poured onto crushed ice/water. The mixture was made basic with 10N sodium hydroxide (50 ml) to pH 12 and extracted with diethyl ether (2×100 ml). The combined organic layers were washed with water (2×100 ml), dried over anhydrous magnesium sulfate, filtered and evaporated under vacuum. The residue was treated with methyl alcohol (20 ml) and heated on a hot water bath (80° C.) until solute dissolved. The flask was covered with aluminum foil (product is light sensitive) and the solution was allowed to stir at room temperature overnight when a yellow solid precipitated. The solid was collected by filtration and dried under vacuum to afford 3.0 g (58%) of m-nitrophencyclidine as fine yellow crystals which were protected from light: mp 81-82° C.

Example 13

Synthesis of meta-Aminophencyclidine

To a stirring solution of m-nitrophencyclidine (3.0 g, $10.4 \times 10^{-3}$ mol) in methyl alcohol (150 ml) was added, under a flow of argon, 10% palladium-carbon (0.5 g) followed by ammonium formate (4.0 g, $6.3 \times 10^{-2}$ mol). The reaction mixture was stirred at room temperature for 2 hours after which time the catalyst was removed by filtration and the solvent was evaporated under vacuum. The residue was treated with 1 N potassium hydroxide solution (30 ml) and extracted with diethyl ether (2×50 ml). The combined organic extracts were washed with water (50 ml), dried over anhydrous magnesium sulfate, filtered and evaporated under vacuum. The residue was dissolved in hexane (20 ml) and the solution was stirred at room temperature overnight when a white solid precipitated. The solid was collected by filtration and dried under vacuum to afford 1.4 g (52%) of m-aminophencyclidine: mp 121-122° C.

Example 14

Synthesis of Acetylthiopropionic Acid

To a stirred solution of 3-mercaptoprionic acid (7 ml, 0.08 moles) and imidazole (5.4 g, 0.08 moles) in tetrahydrofuran (THF, 700 ml) was added dropwise over 15 minutes, under argon, a solution of 1-acetyl imidazole (9.6 g, 0.087 moles) in THF (100 ml). The solution was allowed to stir a further 3 hours at room temperature after which time the THF was removed in vacuo. The residue was treated with ice-cold water (18 ml) and the resulting solution acidified with ice-cold concentrated HCl (14.5 ml) to pH 1.5-2. The mixture was extracted with water (2×50 ml), dried over magnesium sulfate and evaporated. The residual crude yellow oily solid product (10.5 g) was recrystallized from chloroform-hexane to afford 4.8 g (41% yield) acetylthiopropionic acid as a white solid with a melting point of 44-45° C.

Example 15

Synthesis of meta-Acetylthiopropionamide Phencyclidine

To a stirring solution of m-aminophencyclidine (1.4 g, $5.4 \times 10^{-3}$ mol) and acetylthiopropionic acid (0.87 g, $5.8 \times 10^{-3}$ mol) in anhydrous tetrahydrofuran (7 ml) was added dicyclohexylcarbodiimide (1.19 g, $5.8 \times 10^{-3}$ mol). The flask was purged with argon and the solution stirred at room temperature for 2 hours. The mixture was filtered from insoluble dicyclohexylurea and evaporated under vacuum. The residual solid was recrystallized from chloroform/hexane to afford 1.5 g (71%) of m-acetylthiopropionamide phencyclidine as a white crystalline solid: mp 152-4 C.

Example 16

Synthesis of meta-3-Mercaptoproprionamide Phencyclidine meta-Acetylthiopropionamide phencyclidine (0.01 g, $2.57 \times 10^{-5}$ mol) was dissolved in 1.29 ml 0.12 M potassium carbonate in 80% methanol/20% water (v/v). The solution sat at room temperature for 5 min and then 0.2 ml 0.5 M potassium phosphate, pH 7, was immediately added and the solution was adjusted to pH 7-7.5 with hydrochloric acid (1 N). The title compound in solution was used as is to react with BSA-SMCC.

Example 17

Preparation of Phencyclidine Analogue Attached to Bovine Serum Albumin (BSA-PCP)

Bovine serum albumin (BSA, 3.5 ml of 20 mg/ml) was reacted with succinimidyl 4-(N-maleimidomethyl)-cyclohexane-1-carboxylate (SMCC, Pierce Chemical Co.) by adding a solution of 6.7 mg SMCC in 0.3 ml acetonitrile and stirring the solution at room temperature for 1 h while maintaining the pH between 7 and 7.5 with 1 N potassium hydroxide. The protein was separated from unreacted compounds by gel filtration chromatography in 0.1 M potassium phosphate, 0.02 M potassium borate, 0.15 M sodium chloride, pH 7.0. The meta-3-mercaptoproprionamide phencyclidine (0.2 ml of 13 mM) was added to the BSA-maleimide (2 ml at 8.2 mg/ml) and the solution was stirred at room temperature for 4 h. The solution was then dialyzed 3 times against 1000 ml of 10 mM MES, pH 5.5. Recover 1.8 ml BSA-PCP at 8 mg/ml.

Example 18

Preparation of Phencyclidine Analogue Colloidal Gold Conjugate

A solution (4.7 ml) containing BSA (22 mg) and BSA-PCP (5.6 mg) in 10 mM MES, pH 5.5 was added in a bolus to colloidal gold (105 ml) in 10 mM MES, pH 5.5 with rapid stirring. After complete mixing the stirring was stopped and the solution was incubated at room temperature for 1 h. The colloidal gold conjugate was subjected to diafiltration against 50 mM potassium phosphate, 10 mM potassium borate, pH 7, using a tangential flow device (Sartorius Easy Flow, molecular weight cutoff was 100,000) to remove BSA and BSA-PCP which was not bound to colloidal gold. The gold conjugate was diluted for the assay of PCP into a buffered solution containing 10 mg/ml bovine serum albumin at pH 7.5.

Example 19

Preparation of Anti-Phencyclidine Antibody Latex

Surfactant-free polystyrene particles (Interfacial Dynamics Corp., Portland, Oreg.; 0.074 ml of 9.4% solids, 0.4 µm) was added while vortexing to anti-phencyclidine monoclonal antibody (0.926 ml of 5.86 mg/ml in 0.1 M MES, pH 5) and the suspension was incubated at 45° C. for 2 h. The suspension was subjected to centrifugation to pellet the latex particles. The pellet was washed three times by centrifugation and resuspension of the pellet with 10 mM MES, 0.1 mg/ml trehalose, pH 5.5. The final pellet was resuspended in the wash buffer at a solids concentration of 1%.

Example 20

Preparation of Latex-Immobilized Affinity-Purified Goat IgG Antibody Against the Fc Fragment of Mouse IgG (Goat Anti-Mouse Fc Latex)

Affinity-purified goat anti-mouse (Fc (Immunosearch) and polystyrene latex particles (sulfated, 1.07 µm) (Interfacial Dynamics) were incubated separately at 45° C. for one hour, the antibody solution being buffered with 0.1 M 2-(N-morpholino) ethane sulfonic acid at pH 5.5. While vortexing the antibody solution, the suspension of latex particles was added to the antibody solution such that the final concentration of antibody was 0.3 mg/ml and the solution contained 1% latex solids. The suspension was incubated for 2 hours at 45° C. prior to centrifugation of the suspension to pellet the latex particles. The latex pellet was resuspended in 1% bovine serum albumin in phosphate-buffered-saline (PBS) and incubated for one hour at room temperature. Following centrifugation to pellet the latex, the pellet was washed three times by resuspension in PBS and centrifugation. The final pellet was resuspended in PBS containing 0.1% sodium azide at pH 7.0 at a latex concentration of 1% solids.

Example 21

Assay for Phencyclidine Using the Diagnostic Element

The diagnostic element described in Example 10 was used for the assay of phencyclidine (PCP). Urine samples (133 µl) containing 0, 100, 200 and 300 ng/ml PCP were added to tubes containing a lyophilized buffer formulation (containing 10 mM potassium phosphate, 150 mM sodium chloride and 10 mg/ml BSA, pH 8) and phencyclidine analogue colloidal gold conjugate (4 µl) was added and the solution was vortexed. Anti-PCP antibody (2.8 µl of 0.1 mg/ml) was added to each tube and the solutions were vortexed and incubated at room temperature for 5 min. Goat anti-mouse Fc latex (50 ml of a 1% suspension) was added to the tubes, the tubes were vortexed and incubated at room temperature for 10 min. The solutions were then filtered to remove the complex of the PCP analogue gold conjugate:anti-PCP antibody:goat anti-mouse latex from the reaction mixture using a GELMAN ACRODISC® 3 syringe filter (0.45 µm). The filtrates of the reaction mixtures (20 µl) were applied to the diagnostic elements described in example 10. The reaction mixture flowed onto the diagnostic element from the sample reservoir and over the capture zone. An absorbent tissue placed 1 cm after the capture zone removed the used reagent from the diagnostic element. The color density of the capture zones was measured instrumentally using a MINOLTA CHROMA METER CR 241. The _E* values for the 0, 100, 200 and 300 ng/ml samples were 0.69, 9.28, 14.04 and 21.6, respectively.

Example 22

Exemplary Device Configurations

Figure 11:
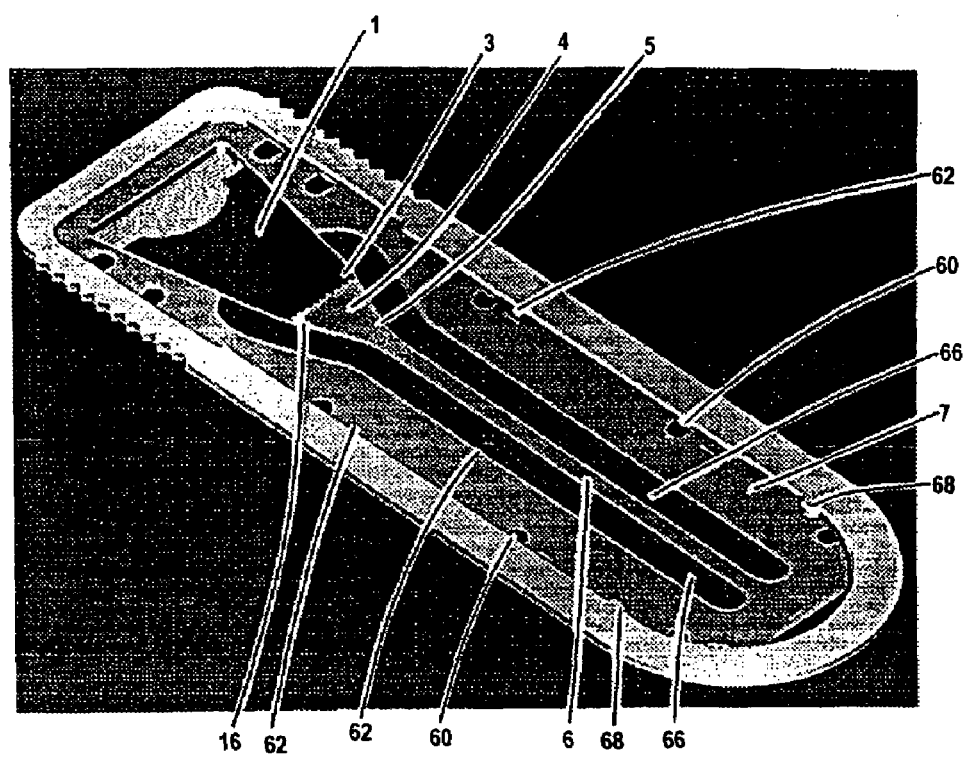
FIG. 11 depicts a preferred embodiment of a device in accordance with the invention.
Figure 12A:
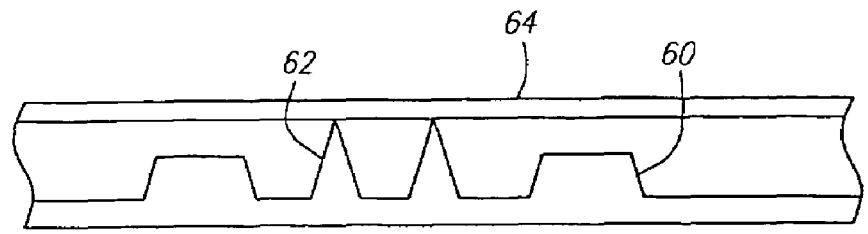
FIGS. 12A-F, respectively depict various embodiments of stops and energy directors in accordance with the invention.
Figure 12B:
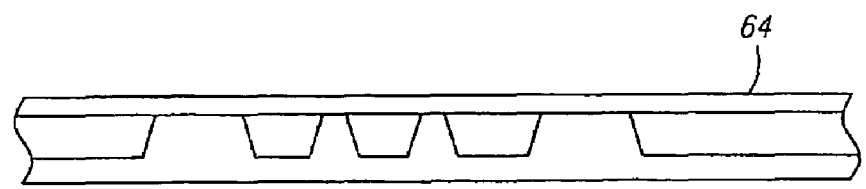
Figure 12C:
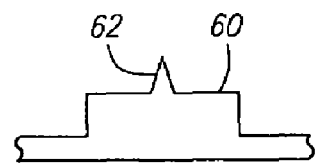
Figure 12D:
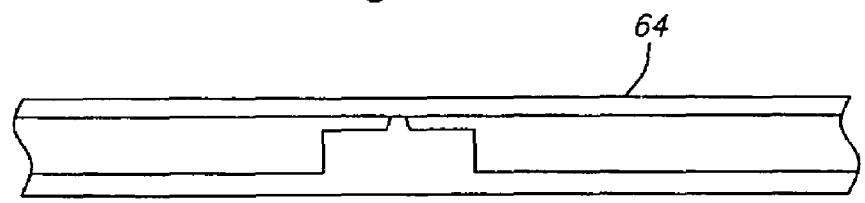
Figure 12E:
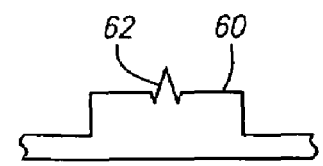
Figure 12F:
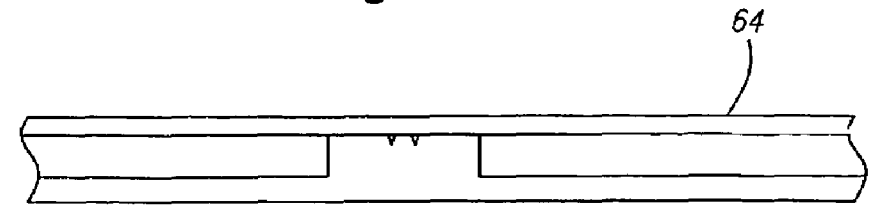

A presently preferred mode of the invention utilizes a device embodiment capable of performing one-step immunoassays. The device preferably comprises a sample addition reservoir 1, a sample reaction barrier 3, a reaction chamber 4, a time gate 5, a diagnostic lane 6, a used reagent reservoir 7, and a lid 64. FIG. 11 depicts a preferred embodiment of the device where the lid is removed to permit illustration of various portions of the device. A lid is not illustrated in FIG. 11, as appreciated by one of ordinary skill in the art, the lid has an access port so that fluid can be introduced into the sample addition reservoir; the lid can also have a vent to facilitate escape of gas as the device fills with liquid. In one embodiment, a vent is located in the lid at an area of the used reagent reservoir.

The sample addition reservoir can comprise a filter (not illustrated) for the separation of plasma from red blood cells or for the separation of debris in the sample from the sample to be assayed and a reservoir for the storage of sample used in the assay device. For additional disclosure concerning filters, see e.g., copending U.S. application Ser. No. 08/704,804, filed 26 Aug. 1996 which is incorporated by reference herein. The sample addition reservoir is in fluid communication with the sample reaction barrier.

The sample reaction barrier can comprise a texture composed of texture structures on a surface thereof. Preferred texture height is about 0.01 to 0.02 mm and width of each texture structure is about 0.09 to 0.20 mm. The distance between adjacent texture structures is about 0.080 to 0.100 mm. The height of the capillary space in the sample reaction barrier is about 0.02 to 0.08 mm. Preferably, the surface of the sample reaction barrier at both edges of the capillary is made hydrophobic to prevent fluid from preferentially flowing at the edges of the capillary. Since the hydrophobic surfaces minimize the flow along the edges of the reaction chamber, these surfaces also direct fluid flow into the reaction chamber, the access to which occurs toward the center of the sample reaction barrier. The sample reaction barrier preferably comprises ten vertical grooves 16 that are in fluid communication with the capillary spaces of the sample reaction barrier and the reaction chamber. The grooves are approximately 0.02 to 0.03 mm high and are spaced about 0.5 to 1.5 mm apart.

The reaction chamber is comprised of a capillary about 0.03 to 1.0 mm high and contains a volume of about 0.2 to 6 µl. Preferably, both inner lid and base surfaces of the reaction chamber capillary space comprise a texture of small texture structures, about 0.015 to 0.03 mm high, with a diameter of 0.05 to 0.1 mm, at a spacing of about 0.1 to 0.3 mm. The reaction chamber is in fluid communication with the time gate. One surface of the reaction chamber adjacent to the time gate comprises grooves to define a flow front perpendicular to the direction of fluid flow. The grooves are oriented substantially perpendicular to the direction of fluid flow. The grooves are generally 0.03 to 0.07 mm high and are spaced 0.08 to 0.12 mm apart. The surface at an edge of the reaction chamber, such as at a corner, is made hydrophobic. As disclosed herein, a hydrophobic region slows flow at the edges of the capillary and prevents fluid from preferentially flowing at the edges.

The time gate is comprised of a capillary about 0.02 to 0.12 mm high. One surface of the time gate is comprised of grooves about 0.03 to 0.07 mm high and spaced about 0.08 to 0.12 mm apart; these grooves are contiguous with similar grooves in the reaction chamber. The grooves are oriented substantially perpendicular to the predominant direction of fluid flow through the device. As disclosed herein, a surface of the time gate is made hydrophobic to delay fluid flow out of the reaction chamber. The time gate is in fluid communication with the diagnostic lane.

Figure 15:
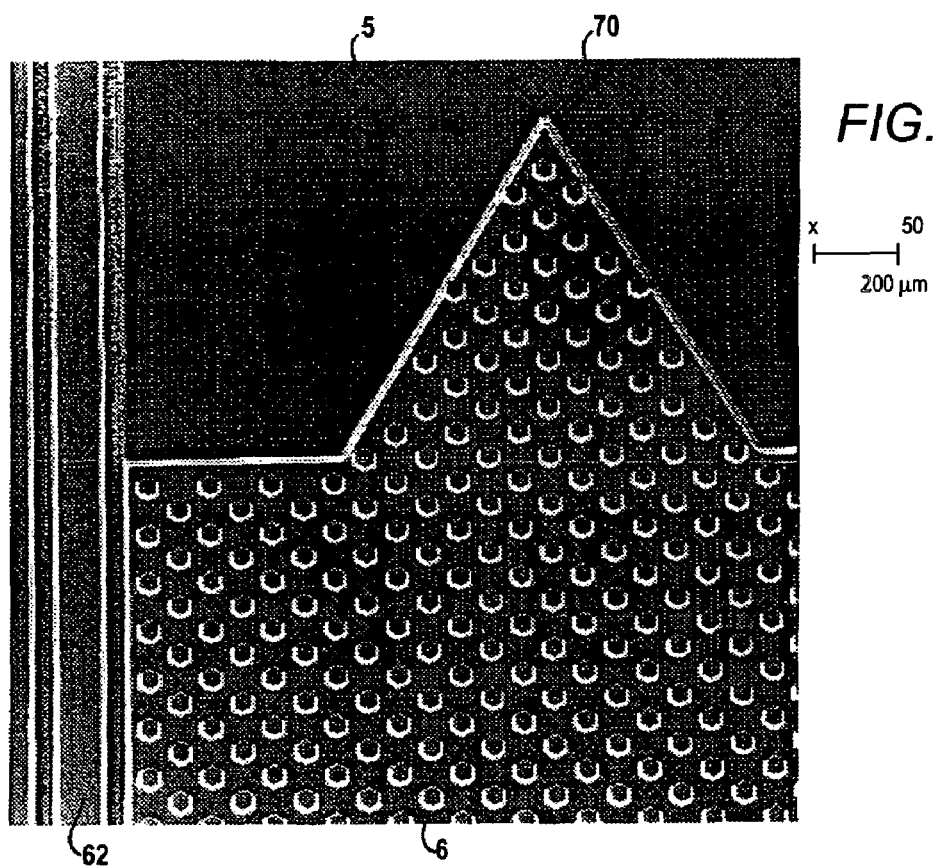
FIG. 15 depicts an electron micrograph of an embodiment of the invention illustrating a time gate 5, a textured diagnostic lane 6, and an energy director 62.

The diagnostic lane/element comprises a capillary preferably about 0.01 to 0.05 mm high and comprises a texture composed of texture structures about 0.01 to 0.02 mm high, 0.03 to 0.07 mm in diameter/width, and spaced about 0.04 to 0.09 mm apart. The volume of the diagnostic lane is about 0.5 to 3 µl. The edges of the capillary in the diagnostic lane are made hydrophobic to slow fluid flow at the edges of the capillary, and to prevent fluid from preferentially flowing at the edges of the capillary. The diagnostic lane is in fluid communication with the used reagent reservoir. As shown in FIG. 15, diagnostic lane 6 preferably begins at a point 70. When the diagnostic lane begins at a point, this allows fluid to enter the lane at a more predictable location, generally the proximal-most location of the diagnostic lane. When fluid enters the lane in a predictable location, this in turn leads to increased predictability of fluid flow in the diagnostic lane itself which allows for uniformity of performance for devices of the same configuration.

The used reagent reservoir preferably comprises a capillary space similar in dimension to the capillary of the diagnostic lane, and is generally of equal or greater volume. It is comprised of a texture comprising texture structures that have a height of about 0.01 to 0.02 mm, widths/diameters of about 0.03 to 0.07 mm which are spaced 0.04 to 0.09 mm apart. The used reagent reservoir can comprise zones that exhibit a color change upon addition of fluid, to visibly indicate to the user that fluid has flowed past that particular zone. For example, the reservoir can contain colored zones that become colorless when fluid comes into contact with them. These colored zones can be made of water soluble dyes, such as green food coloring, that wash away through dissolution by the advancing fluid. Alternatively, the region can contain a zone that develops a color change when fluid has flowed in the region. These zones can consist of receptors that bind a dye label in the sample or bind an enzyme that generates color at the zone. These novel color change features have application in indicating to the user of the test device the extent of completion of the procedure.

Referring now to FIG. 12, a device preferably comprises, generally at the outer edge and in areas where capillary spaces of particular dimension are important, structures referred to as stops 60. The stops serve to establish a capillary space of uniform height, e.g., among various devices manufactured in the same way. A device also preferably comprises energy directors 62. The energy directors also serve to establish a capillary space of uniform height, e.g., among various devices manufactured in the same way, where an energy source such as ultrasonic welding is used to join two parts by melting them together. The energy directors also function to join two pieces of a device, such as joining a lid and a base. As depicted in FIG. 12, an energy director has a height greater than that of a stop. When stops and energy directors are used together, the portion of the energy director that is higher than a stop is induced to melt by an externally applied energy source. As such melting occurs, the two parts being joined come closer together. The closeness of the approximation of the two parts is limited by the stops which, when preferably are used with energy directors, do not melt and thus serve to define a uniform separation of two joined parts. The uniform separation is a capillary space in preferred embodiments of a device in accordance with the invention.

Accordingly, the stops and energy directors are designed to define a capillary space and to maintain a stable union of a lid 64 to the base. Thus, adjacent to the sample addition reservoir, the sample reaction barrier, the reaction chamber, the time gate and the diagnostic lane are energy directors that adjoin the lid to the base, to complete the formation of capillary spaces within the device, and to seal fluid in the capillary spaces. Typically, the lid is ultrasonically welded to the base. Adjacent to the energy directors are stops that are about 0.02 to 0.06 mm high. The stops act to prevent the lid from being attached to the base in a manner that prevents formation of a capillary space; the stops thus serve to define a reproducible capillary space between many devices. The stops are bordered by energy directors so that fluid does not enter the area of the stops.

Furthermore, as depicted in FIG. 11, the device preferably comprises one or more regions of dead space 66 adjacent sides of the diagnostic lane. The dead space(s) allow for detection of a sensible signal, e.g., a color change in the fluorescent or visible spectra, without interference from any signal contained in reactants that are located in a used reagent reservoir or other device region.

The novel use of stops, as described herein, serve to define capillaries or uniform height in devices. As appreciated by one of ordinary skill in the art, the stop height can be varied to establish a variety of capillary spaces in a device. Furthermore, as illustrated in FIG. 12, various stop 60 and energy director 62 embodiments can be prepared in accordance with the present invention. In general, the dimensions of a capillary space designed into a device is determined based on the nature of the sample to be assayed. For example, whole blood or lysed blood has a higher viscosity than plasma or serum. Accordingly, devices were designed with higher capillary gaps to assay whole or lysed blood, these devices had higher gaps than devices for serum or plasma. When whole or lysed blood was used in assays in the devices with the higher capillary gaps, these devices achieved similar assay times and assay characteristics relative to devices configured for use with plasma or serum samples. The devices requiring higher capillary gaps have had correspondingly higher stops.

The stops can be formulated using shims, layers of glue or hardening agents, or they can be molded directly into the part, using injection molding or other conventional molding or fabrication processes. In the case of using silicon chips, stops can be incorporated into devices utilizing photolithography or micromachining techniques.

Figure 13:
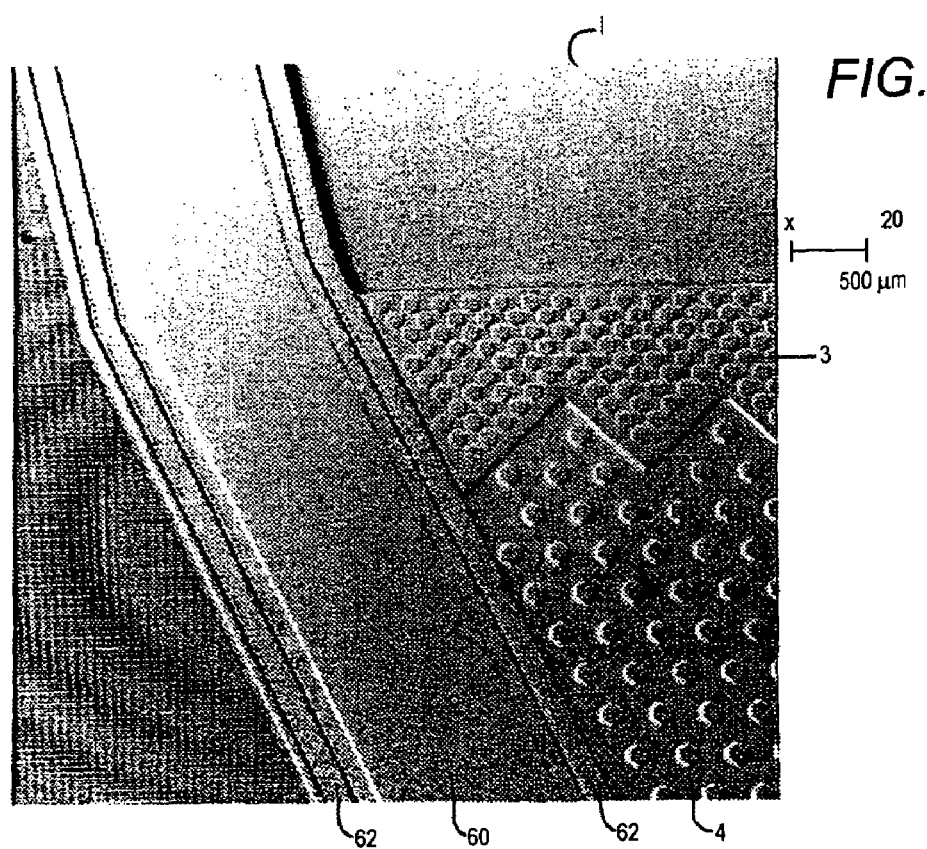
FIG. 13 depicts a electron micrograph of an embodiment of the invention illustrating a sample addition reservoir 1, a textured sample reaction barrier 3, a textured reaction chamber 4, a textured used reagent reservoir 7, a stop 60, a point 70, and energy directors 62.
Figure 14:
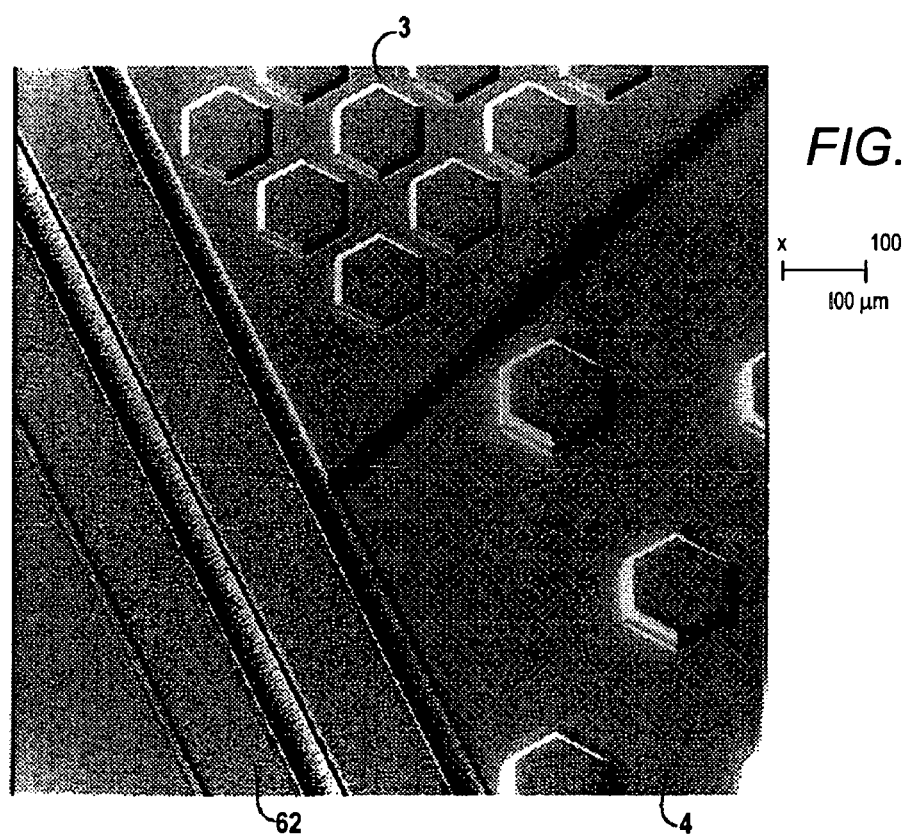
FIG. 14 is an enlarged view of a portion of FIG. 13, illustrating textured sample reaction barrier 3, textured reaction chamber 4, an energy director 62, and stop 60.
Figure 16A:
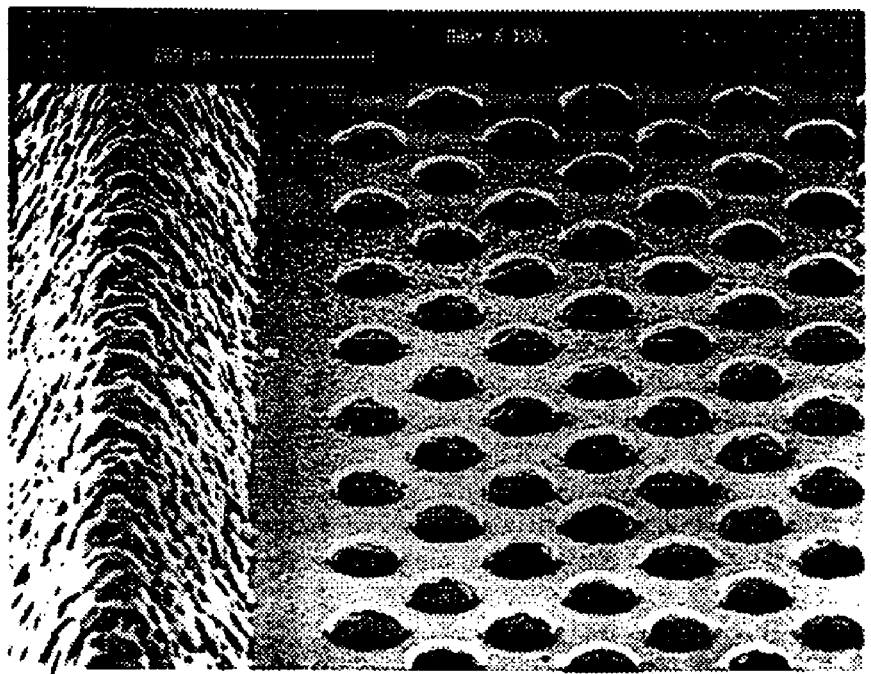
FIG. 16 A-B depict electron micrographs of two views of a textured surface adjacent an energy director 62. The energy director depicted in this embodiment has the form of a ridge.
Figure 16B:
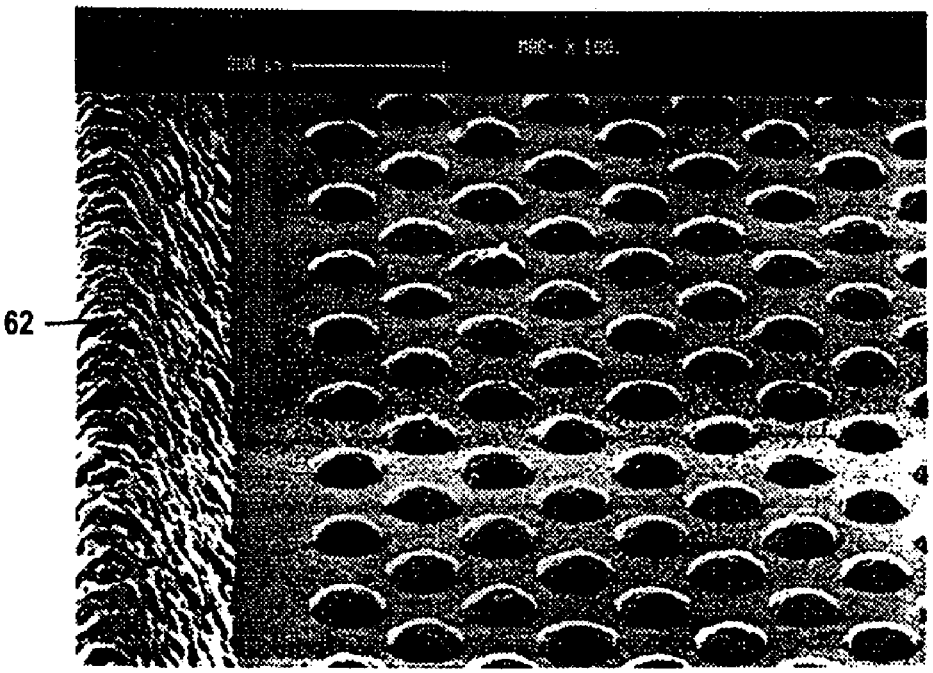

FIG. 13 depicts a electron micrograph of an embodiment of the invention illustrating a sample addition reservoir 1, a textured sample reaction barrier 3, a textured reaction chamber 4, a textured used reagent reservoir 7, a stop 60, and energy directors 62. In this embodiment energy directors 62 and stop 60 collectively constitute a dead space. FIG. 14 is an enlarged view of a portion of FIG. 13, illustrating textured sample reaction barrier 3, textured reaction chamber 4, an energy director 62, and stop 60. FIG. 15 depicts an electron micrograph of an embodiment of the invention illustrating a time gate 5, a textured diagnostic lane 6, and an energy director 62. FIG. 16 A-B depict two views of a textured surface in a capillary space adjacent an energy director 62.

In a further preferred aspect of the invention, depicted in FIG. 11, the device is fabricated to have positioners 68, the lid (not shown) is fabricated to have positioning elements that mate with the asymmetrically placed positioners 68, to ensure that the lid is placed on the device with the correct orientation, so that the surface facing the facing into the device has the appropriate texture. In addition, the lid has a hole at the region of sample addition chamber 1, to permit introduction of fluid into the device.

In a preferred embodiment of an immunoassay device in accordance with the invention, immunoassay reagents are placed on separate surfaces located in a given region of the device. For example, an immunoassay reagent can be immobilized on the lid in the area of the sample reservoir, sample reaction barrier, reaction chamber or diagnostic lane; and a separate immunoassay reagent can be immobilized on the base in an area of the sample reservoir, sample reaction barrier, reaction chamber or diagnostic lane. It is particularly advantageous to place one reagent on a lid and another reagent on a base of the device when the lid and base initially constituted separate pieces that are subsequently attached together in the manufacture of the device. One or more of such immobilized reagents can be diffusible when contacted by fluid.

In accordance with this embodiment of the invention, reagents that could not otherwise be packaged together in a capillary space of a device without the occurrence of adverse cross reactions, can be placed in a device in a single capillary space. For example, if a labeled antibody and a capture antibody were placed together in a capillary space, non-specific interactions can occur in the absence of any target material. Such non-specific interactions lessen the sensitivity of an assay. Fundamental assay types that can utilize reagents localized on separate surfaces in a capillary space include, but are not limited to, competitive immunoassays, sandwich immunoassays and nucleic acid probe assays. Thus, in embodiments where a reagent is dried on a device surface and another reagent is dried on a separate surface of the device, these reagents can diffuse from their respective surfaces upon introduction of fluid to those surfaces. The surfaces having reagent immobilized thereon can be surfaces in a particular chamber of the device or can be surfaces in different regions of the device. The regions can be separate chambers or can be device surfaces that do not delimit a chamber.

Additionally, immunoassay reagents can be immobilized on particles or nanoparticles (collectively referred to herein as particles). Such particles can be placed on a surface, such as a surface delimiting a capillary space, in a device in accordance with the invention. By use of such particles comprising reagents immobilized thereon, one can provide a zone, comprising particles and a surface, where the zone comprises reagents that could not otherwise be provided together. For example, particles comprising immobilized reagents can be placed on a surface where the surface itself comprises a reagent; when the surface is a surface of a capillary space, one or more capillary space surfaces can have a reagent immobilized thereon. Different reagents can be placed on different surfaces. A reagent immobilized by the particles (or on a surface) can be diffusible or non-diffusible when placed in contact with a liquid.

Accordingly, use of a device with the preferred configuration has allowed the performance of one-step immunoassays that simultaneously measure multiple analytes from a biological fluid in an assay time of about 10 minutes.

Closing

Although the foregoing invention has been described in some detail by way of illustration and example, it will be obvious that certain changes or modifications may be practiced within the scope of the appended claims.

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar to equivalent to those described herein can be used in the practice or testing of the invention, the preferred methods and materials are now described. All publications mentioned herein are incorporated herein by reference to describe and disclose specific information for which the reference was cited in connection with.

What is claimed is:

1. An assay device for detecting a plurality of target ligands in a sample, comprising:
   a nonporous textured surface, said nonporous textured surface comprising one or more depressions or protrusions extending between 1 nm and 0.5 mm from said nonporous textured surface; and
   a plurality of discrete capture zones on said surface, each said capture zone comprising receptors immobilized to said surface or immobilized on particles immobilized to said surface, wherein said particle size range is from 1 nm to 5 µm, and wherein said receptors are capable of binding one or more of said plurality of target ligands,
   wherein said capture zones occupy one or more discrete hydrophilic regions of said surface delimited by an adjacent hydrophobic region of said surface.

2. An assay device according to claim 1, wherein each said discrete capture zone comprises receptors independently selected from the group consisting of antibodies, antibody fragments, nucleic acid molecules, and chelators.

3. An assay device according to claim 1, wherein each said discrete capture zone binds a different target ligand from amongst said plurality of target ligands.

4. An assay device according to claim 3, wherein said plurality of target ligands are a plurality of nucleic acid molecules, and each said discrete capture zone comprises a nucleic acid molecule having a nucleotide sequence that is complementary to one of said plurality of nucleic acid molecules.

5. An assay device according to claim 3, wherein each said discrete capture zone comprises an antibody, or a fragment thereof, capable of binding one of said plurality of target ligands.

6. An assay device according to claim 1, wherein one or more of said discrete capture zones comprise one or more particles immobilized to said surface, wherein said receptors are immobilized on said particles.

7. An assay device according to claim 6, wherein said receptors are antibodies, or fragments thereof.

8. An assay device according to claim 6, wherein said surface is a said textured surface, and one or more of said particles are entrapped within depressions and/or between protrusions on the textured surface.

9. An assay device according to claim 6, wherein said particles are selected from the group consisting of latex particles, silica particles, zirconia particles, alumina particles, titania particles, ceria particles, metal sol particles, and polystyrene particles.

10. An assay device according to any one of claims 1-9, wherein said nonporous surface forms a capillary space between said nonporous surface and a second surface spaced at a capillary forming distance from said nonporous surface.

11. An assay device according to any one of claims 1-9, wherein said nonporous surface is not part of a capillary space.

12. An assay device for detecting a plurality of target ligands in a sample, comprising:
   a nonporous textured surface, said nonporous textured surface comprising one or more depressions or protrusions extending between 1 nm and 0.5 mm from said nonporous textured surface; and
   a plurality of discrete capture zones on said surface, each said capture zone comprising receptors immobilized thereon to said surface or immobilized on particles immobilized to said surface, wherein said particle size range is from 1 nm to 5 µm, and wherein said receptors are capable of binding one or more of said plurality of target ligands,
   wherein said capture zones are located in one more diagnostic elements of said surface, said diagnostic elements being hydrophilic and delimited by one or more adjacent hydrophobic regions of said surface.

13. An assay device according to claim 12, wherein each said discrete capture zone comprises receptors independently selected from the group consisting of antibodies, antibody fragments, nucleic acid molecules, and chelators.

14. An assay device according to claim 12, wherein each said discrete capture zone binds a different target ligand from amongst said plurality of target ligands.

15. An assay device according to claim 14, wherein said plurality of target ligands are a plurality of nucleic acid molecules, and each said discrete capture zone comprises a nucleic acid molecule having a nucleotide sequence that is complementary to one of said plurality of nucleic acid molecules.

16. An assay device according to claim 14, wherein each said discrete capture zone comprises an antibody, or a fragment thereof, capable of binding one of said plurality of target ligands.

17. An assay device according to claim 12, wherein one or more of said discrete capture zones comprise one or more particles immobilized to said surface, wherein said receptors are immobilized on said particles.

18. An assay device according to claim 17, wherein said receptors are antibodies, or fragments thereof.

19. An assay device according to claim 17, wherein said surface is said textured surface, and one or more of said particles are entrapped within depressions and/or between protrusions on the textured surface.

20. An assay device according to claim 17, wherein said particles are selected from the group consisting of latex particles, silica particles, zirconia particles, alumina particles, titania particles, ceria particles, metal sol particles, and polystyrene particles.

* * * * *